US008821898B2

(12) United States Patent
Funke et al.

(10) Patent No.: US 8,821,898 B2
(45) Date of Patent: Sep. 2, 2014

(54) ACTIVE COMPOUND COMBINATIONS HAVING INSECTICIDAL AND ACARICIDAL PROPERTIES

(75) Inventors: Christian Funke, Leichlingen (DE); Reiner Fischer, Monheim (DE); Rüdiger Fischer, Pulheim (DE); Heike Hungenberg, Langenfeld (DE); Wolfram Andersch, Bergisch Gladbach (DE); Wolfgang Thielert, Odenthal (DE); Anton Kraus, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 1052 days.

(21) Appl. No.: 10/581,447

(22) PCT Filed: Nov. 20, 2004

(86) PCT No.: PCT/EP2004/013198
§ 371 (c)(1),
(2), (4) Date: Apr. 12, 2007

(87) PCT Pub. No.: WO2005/053405
PCT Pub. Date: Jun. 16, 2005

(65) Prior Publication Data
US 2007/0270416 A1 Nov. 22, 2007

(30) Foreign Application Priority Data
Dec. 4, 2003 (DE) ................................. 103 56 551
May 3, 2004 (DE) .......................... 10 2004 021 566

(51) Int. Cl.
*A61K 9/00* (2006.01)
*A61K 31/54* (2006.01)

(52) U.S. Cl.
USPC ...................................... 424/400; 514/223.8

(58) Field of Classification Search
USPC ....................................................... 514/183
See application file for complete search history.

(56) References Cited

U.S. PATENT DOCUMENTS

| | | |
|---|---|---|
| 3,264,177 A | 8/1966 | Kenaga |
| 4,053,634 A | 10/1977 | Bellina et al. |
| 4,055,661 A | 10/1977 | Bellina et al. |
| 4,070,481 A | 1/1978 | Bellina et al. |
| 4,082,848 A | 4/1978 | Bellina et al. |
| 4,107,325 A | 8/1978 | Bellina et al. |
| 4,115,584 A | 9/1978 | Bellina et al. |
| 4,148,918 A | 4/1979 | Bellina et al. |
| 4,962,126 A | 10/1990 | Drabek |
| 4,985,063 A | 1/1991 | Fisher et al. |
| 5,045,560 A | 9/1991 | Fisher et al. |
| 5,116,836 A | 5/1992 | Fisher et al. |
| 5,225,434 A | 7/1993 | Bertram et al. |
| 5,258,527 A | 11/1993 | Krauskopf et al. |
| 5,462,913 A | 10/1995 | Fisher et al. |
| 5,478,855 A | 12/1995 | Suzuki et al. |
| 5,504,057 A | 4/1996 | Fisher et al. |
| 5,567,671 A | 10/1996 | Fisher et al. |
| 5,622,917 A | 4/1997 | Fisher et al. |
| 5,830,826 A | 11/1998 | Fisher et al. |
| 5,981,567 A | 11/1999 | Fisher et al. |
| 5,994,274 A | 11/1999 | Fisher et al. |
| 6,110,872 A | 8/2000 | Lieb et al. |
| 6,114,362 A | 9/2000 | Dutzmann et al. |
| 6,114,374 A | 9/2000 | Lieb et al. |
| 6,133,296 A | 10/2000 | Lieb et al. |
| 6,140,358 A | 10/2000 | Lieb et al. |
| 6,172,255 B1 | 1/2001 | Fisher et al. |
| 6,200,932 B1 | 3/2001 | Fisher et al. |
| 6,251,830 B1 | 6/2001 | Fisher et al. |
| 6,255,342 B1 | 7/2001 | Lieb et al. |
| 6,288,102 B1 | 9/2001 | Hagemann et al. |
| 6,297,263 B1 | 10/2001 | Dutzmann et al. |
| 6,306,414 B1 | 10/2001 | Koike |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,423,726 B2 | 7/2002 | Dutzmann et al. |
| 6,451,843 B1 | 9/2002 | Lieb et al. |
| 6,458,965 B1 | 10/2002 | Lieb et al. |
| 6,472,419 B1 | 10/2002 | Fisher et al. |
| 6,479,489 B1 | 11/2002 | Fisher et al. |
| 6,479,542 B2 | 11/2002 | Sembo et al. |
| 6,511,942 B1 | 1/2003 | Lieb et al. |
| 6,589,976 B1 | 7/2003 | Fisher et al. |
| 6,608,211 B1 | 8/2003 | Hagemann et al. |

(Continued)

FOREIGN PATENT DOCUMENTS

| | | |
|---|---|---|
| CA | 2072280 A1 | 12/1992 |
| DE | 26 41 343 A1 | 4/1977 |

(Continued)

OTHER PUBLICATIONS

Dialog File 351, Accession No. 1284894, Derwent WPI English language abstract for DE 26 41 343 A1.
Dialog File 351, Accession No. 3940248, Derwent WPI English language abstract for EP 210 487 A1.
Dialog File 351, Accession No. 5386698, Derwent WPI English language abstract for EP 0 355 599 A1.
Dialog File 351, Accession No. 5225712, Derwent WPI English language abstract for EP 0 377 893 A2.
Dialog File 351, Accession No. 5466100, Derwent WPI English language abstract for EP 0 415 211 A2.
Dialog File 351, Accession No. 5637050, Derwent WPI English language abstract for EP 0 442 073 A2.
Dialog File 351, Accession No. 5637204 Derwent WPI English language abstract for EP 0 442 077 A2.

(Continued)

*Primary Examiner* — Snigdha Maewall
(74) *Attorney, Agent, or Firm* — Sterne, Kessler, Goldstein & Fox P.L.L.C.

(57) ABSTRACT

The invention relates to novel insecticidal active compound combinations comprising, firstly, cyclic ketoenols or other insecticidally active compounds and, secondly, further insecticidally active compounds from the group of the anthranilamides, which combinations are highly suitable for controlling animal pests, such as insects and unwanted acarides.

14 Claims, No Drawings

(56) References Cited

U.S. PATENT DOCUMENTS

| | | |
|---|---|---|
| 6,861,391 B1 | 3/2005 | Fisher et al. |
| 7,008,903 B2 | 3/2006 | Dutzmann et al. |
| 7,361,653 B2 | 4/2008 | Sakata et al. |
| 2002/0173529 A1 | 11/2002 | Dutzmann et al. |
| 2003/0216260 A1 | 11/2003 | Ruther et al. |
| 2004/0077500 A1 | 4/2004 | Sakata et al. |
| 2005/0009703 A1 | 1/2005 | Wachendorff-Neumann et al. |
| 2005/0009883 A1 | 1/2005 | Uhr et al. |
| 2005/0101639 A1 | 5/2005 | Ammermann et al. |
| 2006/0004070 A1 | 1/2006 | Wachendorff-Neumann et al. |
| 2006/0014738 A1 | 1/2006 | Wachendorff-Neumann et al. |
| 2006/0035942 A1 | 2/2006 | Wachendorff-Neumann et al. |
| 2006/0079401 A1 | 4/2006 | Dutzmann et al. |
| 2006/0276342 A1 | 12/2006 | Krahmer et al. |
| 2007/0037799 A1 | 2/2007 | Dahmen et al. |
| 2007/0054804 A1 | 3/2007 | Suty-Heinze |
| 2007/0078171 A1 | 4/2007 | Andersch et al. |
| 2007/0142327 A1 | 6/2007 | Funke et al. |
| 2007/0155797 A1 | 7/2007 | Andersch et al. |
| 2007/0203025 A1 | 8/2007 | Bickers et al. |
| 2007/0213396 A1 | 9/2007 | Thielert et al. |
| 2007/0232598 A1 | 10/2007 | Funke et al. |
| 2007/0259787 A1 | 11/2007 | Ohkawara |
| 2007/0270416 A1 | 11/2007 | Funke et al. |
| 2007/0287720 A1 | 12/2007 | Royalty et al. |
| 2008/0027114 A1 | 1/2008 | Funke et al. |
| 2008/0070863 A1 | 3/2008 | Funke et al. |
| 2008/0081807 A1 | 4/2008 | Lieb et al. |
| 2008/0261811 A1 | 10/2008 | Krohn et al. |
| 2008/0269051 A1 | 10/2008 | Suty-Heinze et al. |
| 2008/0269263 A1 | 10/2008 | Dahmen et al. |
| 2008/0274882 A1 | 11/2008 | Krohn et al. |

FOREIGN PATENT DOCUMENTS

| | | | |
|---|---|---|---|
| EP | 0 210 487 A1 | 2/1987 | |
| EP | 0 234 045 A2 | 9/1987 | |
| EP | 0 347 488 A1 | 12/1989 | |
| EP | 0 355 599 A1 | 2/1990 | |
| EP | 0 377 893 A2 | 7/1990 | |
| EP | 0 415 211 A2 | 3/1991 | |
| EP | 0 442 073 A2 | 8/1991 | |
| EP | 0 442 077 A2 | 8/1991 | |
| EP | 0 456 063 A2 | 11/1991 | |
| EP | 0 521 334 A1 | 1/1993 | |
| EP | 0 596 298 A2 | 5/1994 | |
| EP | 0 613 884 A2 | 9/1994 | |
| EP | 0 613 885 A2 | 9/1994 | |
| EP | 0 668 267 A1 | 8/1995 | |
| WO | WO 93/10083 A1 | 5/1993 | |
| WO | WO 93/22297 A1 | 11/1993 | |
| WO | WO 95/01358 A1 | 1/1995 | |
| WO | WO 95/20572 A1 | 8/1995 | |
| WO | WO 95/26954 A1 | 10/1995 | |
| WO | WO 96/35664 A1 | 11/1996 | |
| WO | WO 96/25395 A1 | 12/1996 | |
| WO | WO 97/01535 A1 | 1/1997 | |
| WO | WO 97/02243 A1 | 1/1997 | |
| WO | WO 97/36868 A1 | 10/1997 | |
| WO | WO 97/43275 A2 | 11/1997 | |
| WO | WO 98/05638 A2 | 2/1998 | |
| WO | WO 98/06721 A1 | 2/1998 | |
| WO | WO 98/25928 A1 | 6/1998 | |
| WO | WO 99/16748 A1 | 4/1999 | |
| WO | WO 99/24437 A1 | 5/1999 | |
| WO | WO 99/43649 A1 | 9/1999 | |
| WO | WO 99/48869 A1 | 9/1999 | |
| WO | WO 99/55673 A1 | 11/1999 | |
| WO | WO 01/23354 A1 | 4/2001 | |
| WO | WO 01/74770 A1 | 10/2001 | |
| WO | WO 02/087334 A1 | 11/2002 | |
| WO | WO 03/015518 A1 * | 2/2003 | |
| WO | WO 03/024222 A1 | 3/2003 | |
| WO | WO 2005/079575 A1 | 9/2005 | |
| WO | WO 2005/107468 A1 | 11/2005 | |
| WO | WO 2006/007595 A2 | 1/2006 | |
| WO | WO 2006/108552 A2 | 10/2006 | |

OTHER PUBLICATIONS

Dialog File 351, Accession No. 5720288, Derwent WPI English language abstract for EP 0 456 063 A2.

Dialog File 351, Accession No. 6600806, Derwent WPI English language abstract for EP 0 521 334 A1.

Dialog File 351, Accession No. 6975167, Derwent WPI English language abstract for EP 0 596 298 A2.

Dialog File 351, Accession No. 6979861, Derwent WPI English language abstract for EP 0 613 884 A2.

Dialog File 351, Accession No. 6979862, Derwent WPI English language abstract for EP 0 613 885 A2.

Dialog File 351, Accession No. 7380333, Derwent WPI English language abstract for EP 0 668 267 A1.

Bauer, T.A., et al., "Response of Selected Weed Species to Postemergence Imazethapyr and Bentazon," *Weed Tech.* 9:236-242, The Weed Science Society of America (1995).

Blackshaw, R.E., et al., "Herbicide Combinations for Postemergent Weed Control in Safflower (*Carthamus tinctorius*)," *Weed Tech.* 4:97-104, The Weed Science Society of America (1990).

Blackshaw, R.E., "HOE-39866 Use in Chemical Fallow Systems," *Weed Tech.* 3:420-428, The Weed Science Society of America (1989).

Blackshaw, R.E., "Synergistic Mixes of DPX-A7881 and Clopyralid in Canola (*Brassica napus*)," *Weed Tech.* 3:690-695, The Weed Science Society of America (1989).

Blouin, D.C., et al., "Analysis of Synergistic and Antagonistic Effects of Herbicides Using Nonlinear Mixed-Model Methodology," *Weed Tech.* 18:464-472, The Weed Science Society of America (2004).

Bradley, P.R., et al., "Response of Sorghum (*Sorghum bicolor*) to Atrazine, Ammonium Sulfate, and Glyphosate," *Weed Tech.* 14:15-18, The Weed Science Society of America (2000).

Buker, III, R.S., et al., "Confirmation and Control of a Paraquat-Tolerant Goosegrass (*Eleusine indica*) Biotype," *Weed Tech.* 16:309-313, The Weed Science Society of America (2002).

Burke, I.C., et al., "CGA-362622 Antagonizes Annual Grass Control with Clethodim," *Weed Tech.* 16:749-754, The Weed Science Society of America (2002).

Flint, J.L., et al., "Analyzing Herbicide Interactions, A Statistical Treatment of Colby's Method," *Weed Tech.* 2:304-309, The Weed Science Society of America (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America (1988).

Harker, N. K., and O'Sullivan, P.A., "Synergistic Mixtures of Sethoxydim and Fluazifop on Annual Grass Weeds," *Weed Tech.* 5:310-316, The Weed Science Society of America (1991).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America (1996).

Lanclos, D.Y., et al.,"Glufosinate Tank-Mix Combinations in Glufosinate-Resistant Rice (*Oryza saliva*)," *Weed Tech.* 16:659-663, The Weed Science Society of America (2002).

Norris, J.L., et al., "Weed Control from Herbicide Combinations with Three Formulations of Glyphosate," *Weed Tech.* 15:552-558, The Weed Science Society of America (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).

(56) References Cited

OTHER PUBLICATIONS

Salzman, F.P., and Renner, K.A., "Response of Soybean Combinations of Clomazone, Metribuzin, Linuron, Alachlor, and Atrazine," *Weed Tech*. 6:922-929, The Weed Science Society of America (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech*. 12:463-469, The Weed Science Society of America (1998).

Shaw, D.R. and Arnold, J.C., "Weed Control from Herbicide Combinations with Glyphosate," *Weed Tech*. 16:1-6, The Weed Science Society of America (2002).

Snipes, C.E., and Allen, R.L., "Interaction of Graminicides Applied in Combination with Pyrithiobac," *Weed Tech*. 10:889-892, The Weed Science Society of America (1996).

Wehtje, G. and Walker, R.H., "Interaction of Glyphosate and 2,4-DB for the Control of Selected Morningglory (*Ipomoea spp.*) Species," *Weed Tech*. 11:152-156, The Weed Science Society of America (1997).

Zhang, W., et al., "Fenoxaprop Interactions for Barnyardgrass (*Echinochloa crus-galli*) Control in Rice," *Weed Tech*. 19:293-297, The Weed Science Society of America (2005).

Co-pending U.S. Appl. No. 10/581,348 inventors Funke, C., et al., filed Nov. 20, 2004 (Not Published).

Co-pending U.S. Appl. No. 11/910,659 inventors Wachendorff-Neumann, U., et al., filed Mar. 27, 2007 (Not Published).

Co-pending U.S. Appl. No. 12/515,339 inventors Dutzmann, S., et al., filed May 18, 2009 (Not Published).

International Search Report for International Application No. PCT/EP2004/013198, mailed May 13, 2005, European Patent Office, Rijswijk, The Netherlands.

Co-pending U.S. Appl. No. 12/719,935, inventors Funke, C., et al., filed Mar. 9, 2010 (Not Published).

Co-pending U.S. Appl. No. 12/797,179, inventors Funke, C., et al., filed Jun. 9, 2010 (Not Published).

Oppositions Proceedings for European Patent No. 1 482 798, European Patent Office, dated Nov. 9, 2009; German version.

Oppositions Proceedings for European Patent No. 1 482 798, European Patent Office, dated Nov. 9, 2009; Partial English version.

Patent Owner Response to Opposition for European Patent No. 1 686 857 B1, European Patent Office, dated May 19, 2009; German version.

Patent Owner Response to Opposition for European Patent No. 1 686 857 B1, European Patent Office, dated May 19, 2010; English version translated by RWS Group Ltd, Buckinghamshire, England (Jul. 19, 2010).

Rummens, F.H.A., "An Improved Definition of Synergistic and Antagonistic Effects, " *Weed Science* 23(1):4-6, The Weed Science Society of America, United States (1975).

Office Action mailed on Oct. 13, 2011, in U.S. Appl. No. 12/373,205, filed Nov. 30, 2009.

\* cited by examiner

ACTIVE COMPOUND COMBINATIONS HAVING INSECTICIDAL AND ACARICIDAL PROPERTIES

This application is a 35 U.S.C. §371 U.S. National Phase filing of International Application No. PCT/EP2004/013198, filed Nov. 20, 2004, which claims the benefit of German Patent Application No. 103 56 551.5, filed Dec. 4, 2003 and German Patent Application No. 10 2004 021 566.9, filed May 3, 2004.

The present invention relates to novel active compound combinations comprising, firstly, known cyclic ketoenols and, secondly, further known insecticidally active compounds which combinations are highly suitable for controlling animal pests, such as insects and unwanted acarides.

It is already known that certain cyclic ketoenols have herbicidal, insecticidal and acaricidal properties. The activity of these compounds is good; however, at low application rates it is sometimes unsatisfactory.

Unsubstituted bicyclic 3-arylpyrrolidine-2,4-dione derivatives (EP-A 0 355 599 and EP-A 0 415 211) and substituted monocyclic 3-arylpyrrolidine-2,4-dione derivatives (EP-A 0 377 893 and EP-A 0 442 077) having herbicidal, insecticidal or acaricidal action are known.

Also known are polycyclic 3-arylpyrrolidine-2,4-dione derivatives (EP-A 0 442 073) and 1H-arylpyrrolidinedione derivatives (EP-A 0 456 063, EP-A 0 521 334, EP-A 0 596 298, EP-A 0 613 884, EP-A 0 613 885, WO 94/01 997, WO 95/26 954, WO 95/20 572, EP-A 0 668 267, WO 96/25395, WO 96/35664, WO 97/01535, WO 97/02243, WO 97/36868, WO 97/43275, WO 98/05638, WO 98/06721, WO 98/25928, WO 99/16748, WO 99/24437, WO 99/43649, WO 99/48869 and WO 99/55673, WO 01/23354, WO 01/74770). The activity of these compounds is good; however, at low application rates it is sometimes unsatisfactory.

It is also known that mixtures of phthalamides and further bioactive compounds have insecticidal and/or acaricidal action (WO 02/087334). However, the activity of this mixture is not always optimal.

Furthermore, it is already know that numerous heterocycles, organotin compounds, benzoylureas and pyrethroids have insecticidal and acaricidal properties (cf. WO 93/22297, WO 93/10083, DE-A 26 41 343, EP-A 0 347 488, EP-A 210 487, U.S. Pat. No. 3,364,177 and EP-A 234 045). However, the activity of these compounds is likewise not always satisfactory.

It has now been found that mixtures of compounds of the formula (I) (group 1)

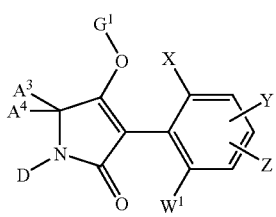
(I)

in which
X represents halogen, alkyl, alkoxy, haloalkyl, haloalkoxy or cyano,
$W^1$, Y and Z independently of one another represent hydrogen, halogen, alkyl, alkoxy, haloalkyl, haloalkoxy or cyano,
$A^3$ represents hydrogen, in each case optionally halogen-substituted alkyl, alkoxyalkyl, saturated, optionally substituted cycloalkyl in which optionally at least one ring atom is replaced by a heteroatom,
$A^4$ represents hydrogen or alkyl,
$A^3$ and $A^4$ furthermore together with the carbon atom to which they are attached represent a saturated or unsaturated, unsubstituted or substituted cycle which optionally contains at least one heteroatom,
D represents hydrogen or an optionally substituted radical from the group consisting of alkyl, alkenyl, alkoxyalkyl, saturated cycloalkyl in which optionally one or more ring members are replaced by heteroatoms,
$A^3$ and D together with the atoms to which they are attached represent a saturated or unsaturated cycle which is unsubstituted or substituted in the $A^3$, D moiety and optionally contains at least one heteroatom,
$G^1$ represents hydrogen (a) or represents one of the groups

(b)

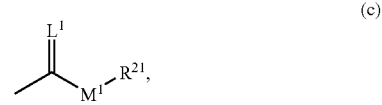
(c)

(d)

(e)

E or
(f)

(g)

E represents a metal ion or an ammonium ion,
$L^1$ represents oxygen or sulfur,
$M^1$ represents oxygen or sulfur,
$R^{20}$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^{21}$ represents in each case optionally halogen-substituted alkyl, alkenyl, alkoxyalkyl, polyalkoxyalkyl or represents in each case optionally substituted cycloalkyl, phenyl or benzyl,
$R^{22}$ represents optionally halogen-substituted alkyl or optionally substituted phenyl,
$R^{23}$ and $R^{24}$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and
$R^{25}$ and $R^{26}$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the nitrogen atom to which they are attached represent an optionally substituted ring which is optionally interrupted by oxygen or sulfur, or an insecticidally active compound (group 2), preferably (2-1) amitraz (known from DE-A 20 61 132)

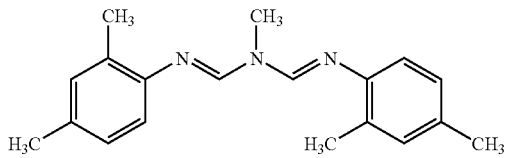

and/or
(2-2) buprofezin (known from DE-A 28 24 126)

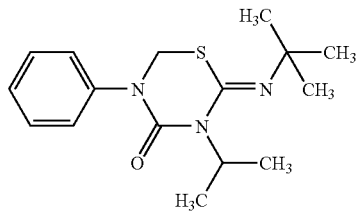 [SMILES: CC(C)N1C(=O)N(c2ccccc2)CS/C1=N\C(C)(C)C]

and/or
(2-3) triazamate (known from EP-A0 213 718)

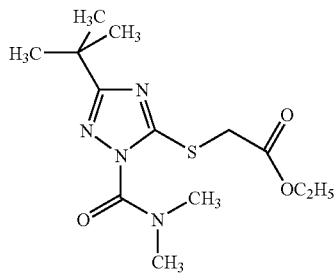

and/or
(2-4) pymetrozine (known from EP-A 0 314 615)

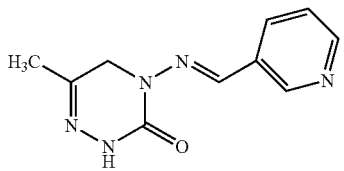 [SMILES: CC1=NNC(=O)N(/N=C/c2cccnc2)C1]

and/or
(2-5) pyriproxifen (known from EP-A 0 128 648)

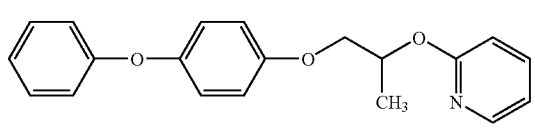 [SMILES: CC(COc1ccc(Oc2ccccc2)cc1)Oc1ccccn1]

and/or
(2-6) flonicamid (known from EP-A 0 580 374)

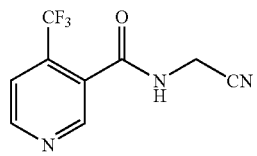 [SMILES: N#CCNC(=O)c1cnccc1C(F)(F)F]

and/or
(2-7) pirimicarb (known from GB 1 181 657)

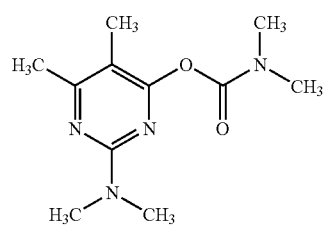

and at least one active compound from the group of the anthranilamides of the formula (II) are synergistically effective and have very good insecticidal and acaricidal properties.

Surprisingly, the insecticidal and/or acaricidal activity of the active compound combinations according to the invention is higher than the sum of the activities of the individual active compounds. Thus, an unforeseeable true synergistic effect is present, and not just an addition of activities. In addition to at least one active compound of the formula (I) or one active compound of group 2 (compounds (2-1) to (2-7)), the active compound combinations according to the invention comprise at least one active compound of the formula (II).

Preference is given to active compound combinations comprising compounds of the formula (I) in which $W^1$ represents hydrogen, $C_1$-$C_4$-alkyl, $C_1$-$C_4$-alkoxy, chlorine, bromine or fluorine, X represents $C_1$-$C_4$-alkyl, $C_1$-$C_4$-alkoxy, $C_1$-$C_4$-haloalkyl, fluorine, chlorine or bromine, Y and Z independently of one another represent hydrogen, $C_1$-$C_4$-alkyl, halogen, $C_1$-$C_4$-alkoxy or $C_1$-$C_4$-haloalkyl, $A^3$ represents hydrogen or in each case optionally halogen-substituted $C_1$-$C_6$-alkyl or $C_3$-$C_8$-cycloalkyl, $A^4$ represents hydrogen, methyl or ethyl, $A^3$ and $A^4$ furthermore together with the carbon atom to which they are attached represent saturated $C_3$-$C_6$-cycloalkyl in which optionally one ring member is replaced by oxygen or sulfur and which is optionally mono- or disubstituted by $C_1$-$C_4$-alkyl, trifluoromethyl or $C_1$-$C_4$-alkoxy, D represents hydrogen, in each case optionally fluorine- or chlorine-substituted $C_1$-$C_6$-alkyl, $C_3$-$C_4$-alkenyl or $C_3$-$C_6$-cycloalkyl, $A^3$ and D together represent optionally methyl-substituted $C_3$-$C_4$-alkanediyl in which optionally one methylene group is replaced by sulfur, $G^1$ represents hydrogen (a) or represents one of the groups

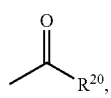

(b)

-continued

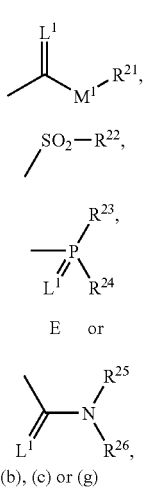

in particular (a), (b), (c) or (g)

E represents a metal ion or an ammonium ion,
$L^1$ represents oxygen or sulfur,
$M^1$ represents oxygen or sulfur,
$R^{20}$ represents in each case optionally halogen-substituted $C_1$-$C_{10}$-alkyl, $C_2$-$C_{10}$-alkenyl, $C_1$-$C_4$-alkoxy-$C_1$-$C_4$-alkyl, $C_1$-$C_4$-alkylthio-$C_1$-$C_4$-alkyl or optionally fluorine-, chlorine-, $C_1$-$C_4$-alkyl- or $C_1$-$C_2$-alkoxy-substituted $C_3$-$C_6$-cycloalkyl,
represents optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl,
represents in each case optionally chlorine- or methyl-substituted pyridyl or thienyl,
$R^{21}$ represents in each case optionally fluorine- or chlorine-substituted $C_1$-$C_{10}$-alkyl, $C_2$-$C_{10}$-alkenyl, $C_1$-$C_4$-alkoxy-$C_2$-$C_4$-alkyl,
represents optionally methyl- or methoxy-substituted $C_5$-$C_6$-cycloalkyl or
represents in each case optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl or benzyl,
$R^{22}$ represents optionally fluorine-substituted $C_1$-$C_4$-alkyl or represents optionally fluorine-, chlorine-, bromine-, $C_1$-$C_4$-alkyl-, $C_1$-$C_4$-alkoxy-, trifluoromethyl-, trifluoromethoxy-, cyano- or nitro-substituted phenyl,
$R^{23}$ represents in each case optionally fluorine- or chlorine-substituted $C_1$-$C_4$-alkyl, $C_1$-$C_4$-alkoxy, $C_1$-$C_4$-alkylamino, $C_1$-$C_4$-alkylthio or represents in each case optionally fluorine-, chlorine-, bromine-, nitro-, cyano-, $C_1$-$C_4$-alkoxy-, trifluoromethoxy-, $C_1$-$C_4$-alkylthio-, $C_1$-$C_4$-haloalkylthio-, $C_1$-$C_4$-alkyl- or trifluoromethyl-substituted phenyl, phenoxy or phenylthio,
$R^{24}$ represents $C_1$-$C_4$-alkoxy or $C_1$-$C_4$-alkylthio,
$R^{25}$ represents $C_1$-$C_6$-alkyl, $C_3$-$C_6$-cycloalkyl, $C_1$-$C_6$-alkoxy, $C_3$-$C_6$-alkenyl, $C_1$-$C_4$-alkoxy-$C_1$-$C_4$-alkyl,
$R^{26}$ represents $C_1$-$C_6$-alkyl, $C_3$-$C_6$-alkenyl or $C_1$-$C_4$-alkoxy-$C_1$-$C_4$-alkyl,
$R^{25}$ and $R^{26}$ furthermore together represent an optionally methyl- or ethyl-substituted $C_3$-$C_6$-alkylene radical in which optionally one carbon atom is replaced by oxygen or sulfur,
and at least one active compound of the formula (II).

In the halogen radicals in the preferred ranges, halogen preferably represents chlorine and fluorine.

Particular preference is given to active compound combinations comprising compounds of the formula (I) in which
$W^1$ represents hydrogen, methyl, ethyl, chlorine, bromine or methoxy,
X represents chlorine, bromine, methyl, ethyl, propyl, isopropyl, methoxy, ethoxy or trifluoromethyl,
Y and Z independently of one another represent hydrogen, fluorine, chlorine, bromine, methyl, ethyl, propyl, isopropyl, trifluoromethyl or methoxy,
$A^3$ represents methyl, ethyl, propyl, isopropyl, butyl, isobutyl, sec-butyl, tert-butyl, cyclopropyl, cyclopentyl or cyclohexyl,
$A^4$ represents hydrogen, methyl or ethyl,
$A^3$ and $A^4$ furthermore together with the carbon atom to which they are attached represent saturated $C_6$-cycloalkyl in which optionally one ring member is replaced by oxygen and which is optionally monosubstituted by methyl, ethyl, methoxy, ethoxy, propoxy or butoxy,
D represents hydrogen, represents methyl, ethyl, propyl, isopropyl, butyl, isobutyl, allyl, cyclopropyl, cyclopentyl or cyclohexyl,
$A^3$ and D together represent optionally methyl-substituted $C_3$-$C_4$-alkanediyl,
$G^1$ represents hydrogen (a) or represents one of the groups

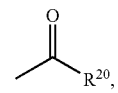

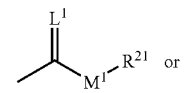

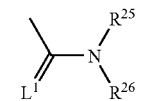

$L^1$ represents oxygen or sulfur,
$M^1$ represents oxygen or sulfur,
$R^{20}$ represents $C_1$-$C_8$-alkyl, $C_2$-$C_4$-alkenyl, methoxymethyl, ethoxymethyl, ethylthiomethyl, cyclopropyl, cyclopentyl or cyclohexyl,
represents phenyl which is optionally mono- to disubstituted by fluorine, chlorine, bromine, cyano, nitro, methyl, ethyl, methoxy, trifluoromethyl or trifluoromethoxy,
represents pyridyl or thienyl, each of which is optionally mono- to disubstituted by chlorine or methyl,
$R^{21}$ represents $C_1$-$C_8$-alkyl, $C_2$-$C_4$-alkenyl, methoxyethyl, ethoxyethyl or represents phenyl or benzyl,
$R^{25}$ and $R^{26}$ independently of one another represent methyl, ethyl or together with the nitrogen atom to which they are attached represent morpholino,
and at least one active compound of the formula (II).

Very particular preference is given to active compound combinations comprising compounds of the formula (I) in which
$W^1$ represents hydrogen or methyl,
X represents chlorine, bromine or methyl,
Y and Z independently of one another represent hydrogen, chlorine, bromine or methyl,
$A^3$ and $A^4$ furthermore together with the carbon atom to which they are attached represent saturated $C_6$-cycloalkyl in which optionally one ring member is replaced by oxygen and is optionally monosubstituted by methyl, methoxy, ethoxy, propoxy or butoxy, D represents hydrogen, $G^1$ represents hydrogen (a) or represents one of the groups

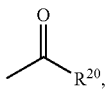

(b)

-continued

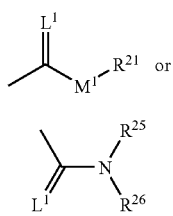

$L^1$ represents oxygen or sulfur,
$M^1$ represents oxygen or sulfur,
$R^{20}$ represents $C_1$-$C_8$-alkyl, $C_2$-$C_4$-alkenyl, methoxymethyl, ethoxymethyl, ethylmethylthio, cyclopropyl, cyclopentyl, cyclohexyl, represents phenyl which is optionally monosubstituted by fluorine, chlorine, bromine, methyl, methoxy, trifluoromethyl, trifluoromethoxy, cyano or nitro, represents pyridyl or thienyl, each of which is optionally monosubstituted by chlorine or methyl, $R^{21}$ represents $C_1$-$C_8$-alkyl, $C_2$-$C_4$-alkenyl, methoxyethyl, ethoxyethyl, phenyl or benzyl, $R^{25}$ and $R^{26}$ independently of one another represent methyl, ethyl or together with the nitrogen atom to which they are attached represent morpholino, and at least one active compound of the formula (II).

Especially preferred are active compound combinations comprising at least one of the following compounds of the formula (I-a)

(I-a)

| Example No. | $W^1$ | X | Y | Z | $R^{27}$ | $G^1$ | m.p. (° C.) |
|---|---|---|---|---|---|---|---|
| I-a-1 | H | Br | 5-$CH_3$ | H | $OCH_3$ | CO-i-$C_3H_7$ | 122 |
| I-a-2 | H | Br | 5-$CH_3$ | H | $OCH_3$ | $CO_2$—$C_2H_5$ | 140-142 |
| I-a-3 | H | $CH_3$ | 5-$CH_3$ | H | $OCH_3$ | H | >220 |
| I-a-4 | H | $CH_3$ | 5-$CH_3$ | H | $OCH_3$ | $CO_2$—$C_2H_5$ | 128 |
| I-a-5 | $CH_3$ | $CH_3$ | 3-Br | H | $OCH_3$ | H | >220 |
| I-a-6 | $CH_3$ | $CH_3$ | 3-Cl | H | $OCH_3$ | H | 219 |
| I-a-7 | H | Br | 4-$CH_3$ | 5-$CH_3$ | $OCH_3$ | CO-i-$C_3H_7$ | 217 |
| I-a-8 | H | $CH_3$ | 4-Cl | 5-$CH_3$ | $OCH_3$ | $CO_2C_2H_5$ | 162 |
| I-a-9 | H | $CH_3$ | 4-$CH_3$ | 5-$CH_3$ | $OCH_3$ | CO—N(morpholino) | oil |
| I-a-10 | $CH_3$ | $CH_3$ | 3-$CH_3$ | 4-$CH_3$ | $OCH_3$ | H | >220 |
| I-a-11 | H | $CH_3$ | 5-$CH_3$ | H | $OC_2H_5$ | CO—N(morpholino) | oil |
| I-a-12 | $CH_3$ | $CH_3$ | 3-Br | H | $OC_2H_5$ | CO-i-$C_3H_7$ | 212-214 |
| I-a-13 | H | $CH_3$ | 4-$CH_3$ | 5-$CH_3$ | $OC_2H_5$ | CO-n-Pr | 134 |
| I-a-14 | H | $CH_3$ | 4-$CH_3$ | 5-$CH_3$ | $OC_2H_5$ | CO-i-Pr | 108 |
| I-a-15 | H | $CH_3$ | 4-$CH_3$ | 5-$CH_3$ | $OC_2H_5$ | CO-c-Pr | 163 | and at least one active compound of the formula (II).

Especially preferred are active compound combinations comprising the compound of the formula (I-a-4)

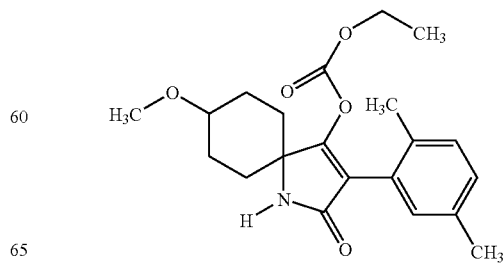

(I-a-4)

and at least one active compound of the formula (II).

Depending inter alia on the nature of the substituents, the compounds of the formula (I) can be present as geometrical and/or optical isomers or isomer mixtures of varying composition which, if desired, may be separated in a customary manner. The present invention provides both the pure isomers and the isomer mixtures, their preparation and use and also compositions comprising them. However, hereinbelow, for the sake of simplicity, only compounds of the formula (I) are referred to, although what is meant are both pure compounds and, if appropriate, also mixtures having varying proportions of isomeric compounds.

Especially preferred are active compound combinations comprising a compound selected from the compounds (2-1) to (2-7) of group 2 and at least one active compound of the formula (II).

The anthranilamides of the formula (II) are likewise known compounds which are known from the following publications or embraced by them:
WO 01/70671, WO 03/015518, WO 03/015519, WO 03/016284, WO 03/016282, WO 03/016283, WO 03/024222, WO 03/062226.

The generic formulae and definitions described in these publications and the individual compounds described therein are expressly incorporated herein by way of reference.

The anthranilamides can be summarized by the formula (II):

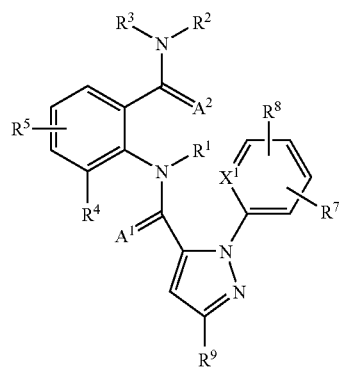

in which
A$^1$ and A$^2$ independently of one another represent oxygen or sulfur,
X$^1$ represents N or CR$^{10}$,
R$^1$ represents hydrogen or represents C$_1$-C$_6$-alkyl, C$_2$-C$_6$-alkenyl, C$_2$-C$_6$-alkynyl or C$_3$-C$_6$-cycloalkyl, each of which is optionally mono- or polysubstituted, where the substituents independently of one another may be selected from the group consisting of R$^6$, halogen, cyano, nitro, hydroxyl, C$_1$-C$_4$-alkoxy, C$_1$-C$_4$-alkylthio, C$_1$-C$_4$-alkylsulfinyl, C$_1$-C$_4$-alkylsulfonyl, C$_2$-C$_4$-alkoxycarbonyl, C$_1$-C$_4$-alkylamino, C$_2$-C$_8$-dialkylamino, C$_3$-C$_6$-cycloalkylamino, (C$_1$-C$_4$-alkyl)-C$_3$-C$_6$-cycloalkylamino and R$^{11}$,
R$^2$ represents hydrogen, C$_1$-C$_6$-alkyl, C$_2$-C$_6$-alkenyl, C$_2$-C$_6$-alkynyl, C$_3$-C$_6$-cycloalkyl, C$_1$-C$_4$-alkoxy, C$_1$-C$_4$-alkylamino, C$_2$-C$_8$-dialkylamino, C$_3$-C$_6$-cycloalkylamino, C$_2$-C$_6$-alkoxycarbonyl or C$_2$-C$_6$-alkylcarbonyl,
R$^3$ represents hydrogen, R$^{11}$ or represents C$_1$-C$_6$-alkyl, C$_2$-C$_6$-alkenyl, C$_2$-C$_6$-alkynyl, C$_3$-C$_6$-cycloalkyl, each of which is optionally mono- or polysubstituted, where the substituents independently of one another may be selected from the group consisting of R$^6$, halogen, cyano, nitro, hydroxyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_2$-C$_6$-alkoxycarbonyl, C$_2$-C$_6$-alkylcarbonyl, C$_3$-C$_6$-trialkylsilyl, R$^{11}$, phenyl, phenoxy and a 5- or 6-membered heteroaromatic ring, where each phenyl, phenoxy and 5- or 6-membered heteroaromatic ring may optionally be substituted and where the substituents independently of one another may be selected from one to three radicals W or one or more radicals R$^{12}$, or
R$^2$ and R$^3$ may be attached to one another and form the ring M,
R$^4$ represents hydrogen, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, cyano, nitro, hydroxyl, C$_1$-C$_4$-alkoxy, C$_1$-C$_4$-haloalkoxy, C$_1$-C$_4$-alkylthio; C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, C$_2$-C$_8$-dialkylamino, C$_3$-C$_6$-cycloalkylamino, C$_3$-C$_6$-trialkylsilyl or represents phenyl, benzyl or phenoxy, each of which is optionally mono- or polysubstituted, where the substituents independently of one another may be selected from the group consisting of C$_1$-C$_4$-alkyl, C$_2$-C$_4$-alkenyl, C$_2$-C$_4$-alkynyl, C$_3$-C$_6$-cycloalkyl, C$_1$-C$_4$-haloalkyl, C$_2$-C$_4$-haloalkenyl, C$_2$-C$_4$-haloalkynyl, C$_3$-C$_6$-halocycloalkyl, halogen, cyano, nitro, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-alkylamino, C$_2$-C$_8$-dialkylamino, C$_3$-C$_6$-cycloalkylamino, C$_3$-C$_6$-(alkyl)cycloalkylamino, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl and C$_3$-C$_6$-trialkylsilyl,
R$^5$ and R$^8$ in each case independently of one another represent hydrogen, halogen or represent in each case optionally substituted C$_1$-C$_4$-alkyl, C$_1$-C$_4$-haloalkyl, R$^{12}$, G, J, —OJ, —OG, —S(O)$_p$-J, —S(O)$_p$-G, —S(O)$_p$-phenyl, where the substituents independently of one another may be selected from one to three radicals W or from the group consisting of R$^{12}$, C$_1$-C$_{10}$-alkyl, C$_2$-C$_6$-alkenyl, C$_2$-C$_6$-alkynyl, C$_1$-C$_4$-alkoxy and C$_1$-C$_4$-alkylthio, where each substituent may be substituted by one or more substituents independently of one another selected from the group consisting of G, J, R$^6$, halogen, cyano, nitro, amino, hydroxyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, C$_2$-C$_8$-dialkylamino, C$_3$-C$_6$-trialkylsilyl, phenyl and phenoxy, where each phenyl or phenoxy ring may optionally be substituted and where the substituents independently of one another may be selected from one to three radicals W or one or more radicals R$^{12}$,
G in each case independently of one another represent a 5- or 6-membered non-aromatic carbocyclic or heterocyclic ring which may optionally contain one or two ring members from the group consisting of C(═O), SO and S(═O)$_2$ and which may optionally be substituted by one to four substituents independently of one another selected from the group consisting of C$_1$-C$_2$-alkyl, halogen, cyano, nitro and C$_1$-C$_2$-alkoxy, or independently of one another represent C$_2$-C$_6$-alkenyl, C$_2$-C$_6$-alkynyl, C$_3$-C$_7$-cycloalkyl, (cyano)-C$_3$-C$_7$-cycloalkyl, (C$_1$-C$_4$-alkyl)-C$_3$-C$_6$-cycloalkyl, (C$_3$-C$_6$-cycloalkyl)-C$_1$-C$_4$-alkyl, where each cycloalkyl, (alkyl)cycloalkyl and (cycloalkyl)alkyl may optionally be substituted by one or more halogen atoms,
J in each case independently of one another represent an optionally substituted 5- or 6-membered heteroaromatic ring, where the substituents independently of one another may be selected from one to three radicals W or one or more radicals $R^{12}$, $R^6$ independently of one another represent —C(=$E^1$)$R^{19}$, LC(=$E^1$)$R^{19}$, —C(=$E^1$)L$R^{19}$, -LC(=$E^1$)L$R^{19}$, —OP(=Q)(O$R^{19}$)$_2$, —SO$_2$L$R^{18}$ or -LSO$_2$L$R^{19}$, where each $E^1$ independently of one another represents O, S, N—$R^{15}$, N—O$R^{15}$, N—N($R^{15}$)$_2$, N—S=O, N—CN or N—NO$_2$, $R^7$ represents hydrogen, $C_1$-$C_4$-alkyl, $C_1$-$C_4$-haloalkyl, halogen, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio; $C_1$-$C_4$-haloalkylsulfinyl, $C_1$-$C_4$-haloalkylsulfonyl, $R^9$ represents $C_1$-$C_4$-haloalkyl, $C_1$-$C_4$-haloalkoxy, $C_1$-$C_4$-haloalkylsulfinyl or halogen, $R^{10}$ represents hydrogen, $C_1$-$C_4$-alkyl, $C_1$-$C_4$-haloalkyl, halogen, cyano or $C_1$-$C_4$-haloalkoxy, $R^{11}$ in each case independently of one another represents in each case optionally mono- to trisubstituted $C_1$-$C_6$-alkylthio, $C_1$-$C_6$-alkylsulfenyl, $C_1$-$C_6$-haloalkylthio, $C_1$-$C_6$-haloalkylsulfenyl, phenylthio or phenylsulfenyl, where the substituents independently of one another may be selected from the list W, —S(O)$_n$N($R^{16}$)$_2$, —C(=Q)$R^{13}$, -L(C=O)$R^{14}$, —S(C=O)L$R^{14}$, —C(=O)L$R^{13}$, —S(O)$_n$N$R^{13}$C(=O)$R^{13}$, —S(O)$_n$N$R^{13}$C(=O))L$R^{14}$ or —S(O)$_n$N$R^{13}$S(O)$_2$L$R^{14}$, L in each case independently of one another represents O, N$R^{18}$ or S, $R^{12}$ in each case independently of one another represents —B(O$R^{17}$)$_2$, amino, SH, thiocyanato, $C_3$-$C_8$-trialkylsilyloxy, $C_1$-$C_4$-alkyl disulfide, —SF$_5$, —C(=$E^1$)$R^{19}$, -LC(=$E^1$)$R^{19}$, —C(=$E^1$)L$R^{19}$, -LC(=$E^1$)L$R^{19}$, —OP(=Q)(O$R^{19}$)$_2$, —SO$_2$L$R^{19}$ or -LSO$_2$L$R^{19}$, Q represents O or S, $R^{13}$ in each case independently of one another represent hydrogen or represent in each case optionally mono- or polysubstituted $C_1$-$C_6$-alkyl, $C_2$-$C_6$-alkenyl, $C_2$-$C_6$-alkynyl or $C_3$-$C_6$-cycloalkyl, where the substituents independently of one another may be selected from the group consisting of $R^6$, halogen, cyano, nitro, hydroxyl, $C_1$-$C_4$-alkoxy, $C_1$-$C_4$-alkylsulfinyl, $C_1$-$C_4$-alkylsulfonyl, $C_1$-$C_4$-alkylamino, $C_2$-$C_8$-alkylamino, $C_3$-$C_6$-cycloalkylamino or ($C_1$-$C_4$-alkyl)-$C_3$-$C_6$-cycloalkylamino, $R^{14}$ in each case independently of one another represent in each case optionally mono- or polysubstituted $C_1$-$C_{20}$-alkyl, $C_2$-$C_{20}$-alkenyl, $C_2$-$C_{20}$-alkynyl or $C_3$-$C_6$-cycloalkyl, where the substituents independently of one another may be selected from the group consisting of $R^6$, halogen, cyano, nitro, hydroxyl, $C_1$-$C_4$-alkoxy, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino and ($C_1$-$C_4$-alkyl)-$C_3$-$C_6$-cycloalkylamino or represent optionally substituted phenyl, where the substituents independently of one another may be selected from one to three radicals W or one or more radicals $R^{12}$, $R^{15}$ in each case independently of one another represent hydrogen or represent in each case optionally mono- or polysubstituted $C_1$-$C_6$-haloalkyl or $C_1$-$C_6$-alkyl, where the substituents independently of one another may be selected from the group consisting of cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_2$-$C_6$-alkoxycarbonyl, $C_2$-$C_6$-alkylcarbonyl, $C_3$-$C_6$-trialkylsilyl and optionally substituted phenyl, where the substituents independently of one another may be selected from one to three radicals W or one or more radicals $R^{12}$, or N($R^{15}$)$_2$ represents a cycle which forms the ring M, $R^{16}$ represents $C_1$-$C_{12}$-alkyl or $C_1$-$C_{12}$-haloalkyl, or N($R^{16}$)$_2$ represents a cycle which forms the ring M, $R^{17}$ in each case independently of one another represent hydrogen or $C_1$-$C_4$-alkyl, or B(O$R^{17}$)$_2$ represents a ring in which the two oxygen atoms are attached via a chain having two to three carbon atoms which are optionally substituted by one or two substituents independently of one another selected from the group consisting of methyl and $C_2$-$C_6$-alkoxycarbonyl, $R^{18}$ in each case independently of one another represent hydrogen, $C_1$-$C_6$-alkyl or $C_1$-$C_6$-haloalkyl, or N($R^{13}$)($R^{18}$) represents a cycle which forms the ring M, $R^{19}$ in each case independently of one another represent hydrogen or represent in each case optionally mono- or polysubstituted $C_1$-$C_6$-alkyl, where the substituents independently of one another may be selected from the group consisting of cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, CO$_2$H, $C_2$-$C_6$-alkoxycarbonyl, $C_2$-$C_6$-alkylcarbonyl, $C_3$-$C_6$-trialkylsilyl and optionally substituted phenyl, where the substituents independently of one another may be selected from one to three radicals W, $C_1$-$C_6$-haloalkyl, $C_3$-$C_6$-cycloalkyl or phenyl or pyridyl, each of which is optionally mono- to trisubstituted by W, M in each case represents an optionally mono- to tetrasubstituted ring which, in addition to the nitrogen atom attached to the substituent pair $R^{13}$ and $R^{18}$, ($R^{15}$)$_2$ or ($R^{16}$)$_2$, contains two to six carbon atoms and optionally additionally a further nitrogen, sulfur or oxygen atom, where the substituents independently of one another may be selected from the group consisting of $C_1$-$C_2$-alkyl, halogen, cyano, nitro and $C_1$-$C_2$-alkoxy, W in each case independently of one another represent $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, nitro, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino, ($C_1$-$C_4$-alkyl)-$C_3$-$C_6$-cycloalkylamino, $C_2$-$C_4$-alkylcarbonyl, $C_2$-$C_6$-alkoxycarbonyl, CO$_2$H, $C_2$-$C_6$-alkylaminocarbonyl, $C_3$-$C_8$-dialkylaminocarbonyl or $C_3$-$C_6$-trialkylsilyl, n in each case independently of one another represent 0 or 1, p in each case independently of one another represent 0, 1 or 2, where, if (a) $R^5$ represents hydrogen, $C_1$-$C_6$-alkyl, $C_1$-$C_6$-haloalkyl, $C_2$-$C_6$-haloalkenyl, $C_2$-$C_6$-haloalkynyl, $C_1$-$C_4$-haloalkoxy, $C_1$-$C_4$-haloalkylthio or halogen and (b) $R^8$ represents hydrogen, $C_1$-$C_6$-alkyl, $C_1$-$C_6$-haloalkyl, $C_2$-$C_6$-haloalkenyl, $C_2$-$C_6$-haloalkynyl, $C_1$-$C_4$-haloalkoxy, $C_1$-$C_4$-haloalkylthio, halogen, $C_2$-$C_4$-alkylcarbonyl, $C_2$-$C_6$-alkoxycarbonyl, $C_2$-$C_6$-alkylaminocarbonyl or $C_3$-$C_8$ dialkylaminocarbonyl, (c) at least one substituent selected from the group consisting of $R^6$, $R^{11}$ and $R^{12}$ is present and (d) if $R^{12}$ is not present, at least one of the radicals $R^6$ and $R^{11}$ is different from $C_2$-$C_6$-alkylcarbonyl, $C_2$-$C_6$ alkoxycarbonyl, $C_2$-$C_6$-alkylaminocarbonyl and $C_3$-$C_8$-dialkylaminocarbonyl.

The compounds of the general formula (II) comprise N-oxides and salts.

Depending inter alia on the nature of the substituents, the compounds of the formula (II) can be present as geometrical and/or optical isomers or isomer mixtures of varying composition which, if desired, may be separated in a customary manner. The present invention provides both the pure isomers and the isomer mixtures, their preparation and use and also compositions comprising them. However, hereinbelow, for the sake of simplicity, only compounds of the formula (II) are referred to, although what is meant are both pure compounds and, if appropriate, also mixtures having varying proportions of isomeric compounds.

Preference is given to active compound combinations comprising compounds of the formula (II-1)

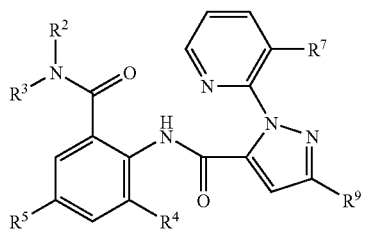

(II-1)

in which
$R^2$ represents hydrogen or $C_1$-$C_6$-alkyl,
$R^3$ represents $C_1$-$C_6$-alkyl which is optionally substituted by one $R^6$,
$R^4$ represents $C_1$-$C_4$-alkyl, $C_1$-$C_2$-haloalkyl, $C_1$-$C_2$-haloalkoxy or halogen,
$R^5$ represents hydrogen, $C_1$-$C_4$-alkyl, $C_1$-$C_2$-haloalkyl, $C_1$-$C_2$-haloalkoxy or halogen,
$R^6$ represents. —$C(=E^2)R^{19}$, -$LC(=E^2)R^{19}$, —$C(=E^2)LR^{19}$ or -$LC(=E^2)LR^{19}$, where each $E^2$ independently of one another represents O, S, N—$R^{15}$, N—$OR^{15}$, N—$N(R^{15})_2$, and each L independently of one another represents O or $NR^{18}$,
$R^7$ represents $C_1$-$C_4$-haloalkyl or halogen,
$R^9$ represents $C_1$-$C_2$-haloalkyl, $C_1$-$C_2$-haloalkoxy, $S(O)_p$—$C_1$-$C_2$-haloalkyl or halogen,
$R^{15}$ in each case independently of one another represent hydrogen or represent in each case optionally substituted $C_1$-$C_6$-haloalkyl or $C_1$-$C_6$-alkyl, where the substituents independently of one another may be selected from the group consisting of cyano, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl and $C_1$-$C_4$-haloalkylsulfonyl,
$R^{18}$ in each case represents hydrogen or $C_1$-$C_4$-alkyl,
$R^{19}$ in each case independently of one another represent hydrogen or $C_1$-$C_6$-alkyl,
p independently of one another represent 0, 1, 2.

In the radical definitions mentioned as being preferred, halogen represents fluorine, chlorine, bromine and iodine, in particular fluorine, chlorine and bromine.

Particular preference is given to active compound combinations comprising compounds of the formula (II-1) in which
$R^2$ represents hydrogen or methyl,
$R^3$ represents $C_1$-$C_4$-alkyl (in particular methyl, ethyl, n-, isopropyl, n-, iso-, sec-, tert-butyl),
$R^4$ represents methyl, trifluoromethyl, trifluoromethoxy, fluorine, chlorine, bromine or iodine,
$R^5$ represents hydrogen, fluorine, chlorine, bromine, iodine, trifluoromethyl or trifluoroethoxy,
$R^7$ represents chlorine or bromine,
$R^9$ represents trifluoromethyl, chlorine, bromine, difluoromethoxy or trifluoroethoxy.

Very particular preference is given to active compound combinations comprising the following compounds of the formula (II-1):

(II-1)

| Example No. | $R^2$ | $R^3$ | $R^4$ | $R^5$ | $R^7$ | $R^9$ | m.p. (° C.) |
|---|---|---|---|---|---|---|---|
| II-1-1 | H | Me | Me | Cl | Cl | $CF_3$ | 185-186 |
| II-1-2 | H | Me | Me | Cl | Cl | $OCH_2CF_3$ | 207-208 |
| II-1-3 | H | Me | Me | Cl | Cl | Cl | 225-226 |
| II-1-4 | H | Me | Me | Cl | Cl | Br | 162-164 |
| II-1-5 | H | Me | Cl | Cl | Cl | $CF_3$ | 155-157 |
| II-1-6 | H | Me | Cl | Cl | Cl | $OCH_2CF_3$ | 192-195 |
| II-1-7 | H | Me | Cl | Cl | Cl | Cl | 205-206 |
| II-1-8 | H | Me | Cl | Cl | Cl | Br | 245-246 |
| II-1-9 | H | i-Pr | Me | Cl | Cl | $CF_3$ | 195-196 |
| II-1-10 | H | i-Pr | Me | Cl | Cl | $OCH_2CF_3$ | 217-218 |
| II-1-11 | H | i-Pr | Me | Cl | Cl | Cl | 173-175 |
| II-1-12 | H | i-Pr | Me | Cl | Cl | Br | 159-161 |
| II-1-13 | H | i-Pr | Cl | Cl | Cl | $CF_3$ | 200-201 |
| II-1-14 | H | i-Pr | Cl | Cl | Cl | $OCH_2CF_3$ | 232-235 |
| II-1-15 | H | i-Pr | Cl | Cl | Cl | Cl | 197-199 |
| II-1-16 | H | i-Pr | Cl | Cl | Cl | Br | 188-190 |
| II-1-17 | H | Et | Me | Cl | Cl | $CF_3$ | 163-164 |
| II-1-18 | H | Et | Me | Cl | Cl | $OCH_2CF_3$ | 205-207 |
| II-1-19 | H | Et | Me | Cl | Cl | Cl | 199-200 |
| II-1-20 | H | Et | Me | Cl | Cl | Br | 194-195 |
| II-1-21 | H | Et | Cl | Cl | Cl | $CF_3$ | 201-202 |
| II-1-22 | H | Et | Cl | Cl | Cl | Cl | 206-208 |
| II-1-23 | H | Et | Cl | Cl | Cl | Br | 214-215 |
| II-1-24 | H | t-Bu | Me | Cl | Cl | $CF_3$ | 223-225 |
| II-1-25 | H | t-Bu | Me | Cl | Cl | Cl | 163-165 |
| II-1-26 | H | t-Bu | Me | Cl | Cl | Br | 159-161 |
| II-1-27 | H | t-Bu | Cl | Cl | Cl | $CF_3$ | 170-172 |
| II-1-28 | H | t-Bu | Cl | Cl | Cl | Cl | 172-173 |
| II-1-29 | H | t-Bu | Cl | Cl | Cl | Br | 179-180 |
| II-1-30 | H | Me | Me | Br | Cl | $CF_3$ | 222-223 |
| II-1-31 | H | Et | Me | Br | Cl | $CF_3$ | 192-193 |
| II-1-32 | H | i-Pr | Me | Br | Cl | $CF_3$ | 197-198 |
| II-1-33 | H | t-Bu | Me | Br | Cl | $CF_3$ | 247-248 |
| II-1-34 | H | Me | Me | Br | Cl | Cl | 140-141 |
| II-1-35 | H | Et | Me | Br | Cl | Cl | 192-194 |
| II-1-36 | H | i-Pr | Me | Br | Cl | Cl | 152-153 |
| II-1-37 | H | t-Bu | Me | Br | Cl | Cl | 224-225 |
| II-1-38 | H | Me | Me | Br | Cl | Br | 147-149 |
| II-1-39 | H | Et | Me | Br | Cl | Br | 194-196 |
| II-1-40 | H | i-Pr | Me | Br | Cl | Br | 185-187 |
| II-1-41 | H | t-Bu | Me | Br | Cl | Br | 215-221 |
| II-1-42 | H | Me | Me | I | Cl | $CF_3$ | 199-200 |
| II-1-43 | H | Et | Me | I | Cl | $CF_3$ | 199-200 |
| II-1-44 | H | i-Pr | Me | I | Cl | $CF_3$ | 188-189 |
| II-1-45 | H | t-Bu | Me | I | Cl | $CF_3$ | 242-243 |
| II-1-46 | H | Me | Me | I | Cl | Cl | 233-234 |
| II-1-47 | H | Et | Me | I | Cl | Cl | 196-197 |
| II-1-48 | H | i-Pr | Me | I | Cl | Cl | 189-190 |
| II-1-49 | H | t-Bu | Me | I | Cl | Cl | 228-229 |
| II-1-50 | H | Me | Me | I | Cl | Br | 229-230 |
| II-1-51 | H | iPr | Me | I | Cl | Br | 191-192 |
| II-1-52 | H | Me | Br | Br | Cl | $CF_3$ | 162-163 |
| II-1-53 | H | Et | Br | Br | Cl | $CF_3$ | 188-189 |
| II-1-54 | H | i-Pr | Br | Br | Cl | $CF_3$ | 192-193 |
| II-1-55 | H | t-Bu | Br | Br | Cl | $CF_3$ | 246-247 |
| II-1-56 | H | Me | Br | Br | Cl | Cl | 188-190 |
| II-1-57 | H | Et | Br | Br | Cl | Cl | 192-194 |

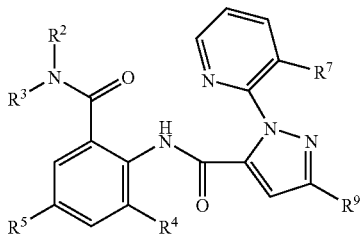

(II-1)

| Example No. | R² | R³ | R⁴ | R⁵ | R⁷ | R⁹ | m.p. (° C.) |
|---|---|---|---|---|---|---|---|
| II-1-58 | H | i-Pr | Br | Br | Cl | Cl | 197-199 |
| II-1-59 | H | t-Bu | Br | Br | Cl | Cl | 210-212 |
| II-1-60 | H | Me | Br | Br | Cl | Br | 166-168 |
| II-1-61 | H | Et | Br | Br | Cl | Br | 196-197 |
| II-1-62 | H | i-Pr | Br | Br | Cl | Br | 162-163 |
| II-1-63 | H | t-Bu | Br | Br | Cl | Br | 194-196 |
| II-1-64 | H | t-Bu | Cl | Br | Cl | CF₃ | 143-145 |
| II-1-65 | Me | Me | Br | Br | Cl | Cl | 153-155 |
| II-1-66 | Me | Me | Me | Br | Cl | CF₃ | 207-208 |
| II-1-67 | Me | Me | Cl | Cl | Cl | Cl | 231-232 |
| II-1-68 | Me | Me | Br | Br | Cl | Br | 189-190 |
| II-1-69 | Me | Me | Cl | Cl | Cl | Br | 216-218 |
| II-1-70 | Me | Me | Cl | Cl | Cl | CF₃ | 225-227 |
| II-1-71 | Me | Me | Br | Br | Cl | CF₃ | 228-229 |
| II-1-72 | H | i-Pr | Me | H | Cl | CF₃ | 237-239 | and also an active compound of the formula (I) (group 1) or of group 2 selected from the compounds (2-1) to (2-7).

Especially preferred are active compound combinations comprising a compound of the following formulae

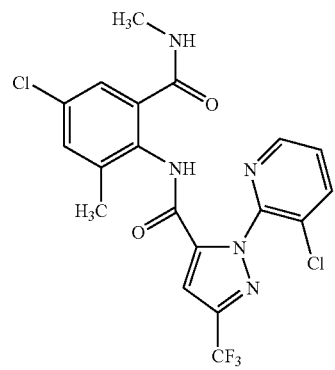

(II-1-1)

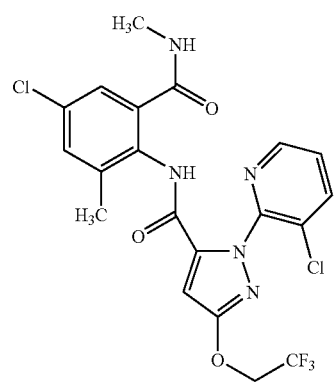

(II-1-2)

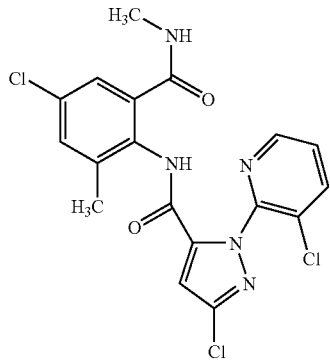

(II-1-3)

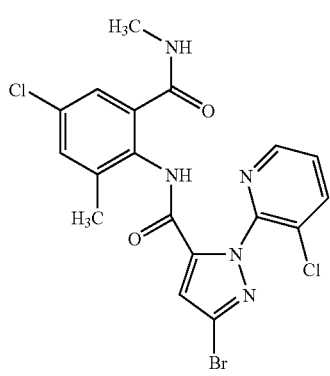

(II-1-4)

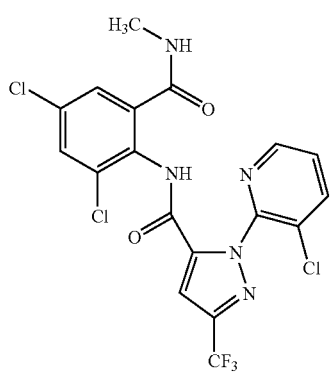

(II-1-5)

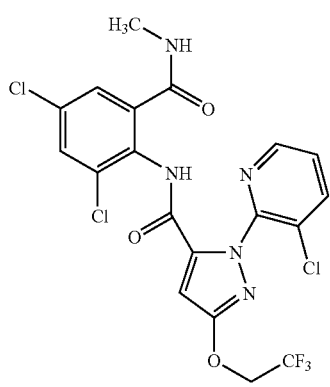

(II-1-6)

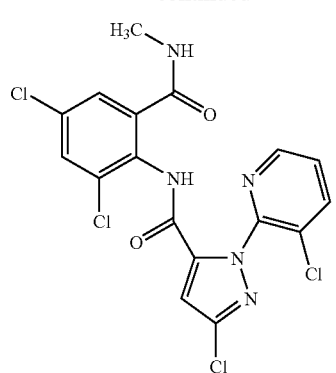
(II-1-7)
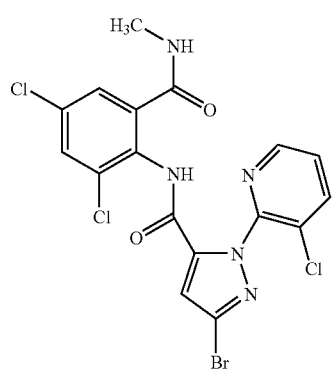
(II-1-8)
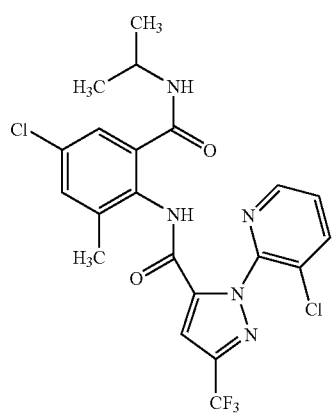
(II-1-9)
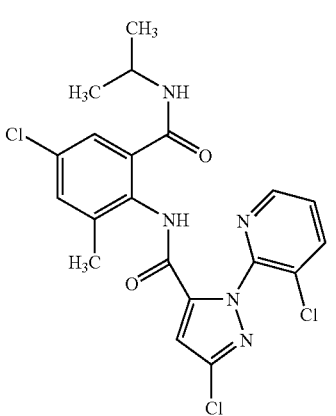
(II-1-11)
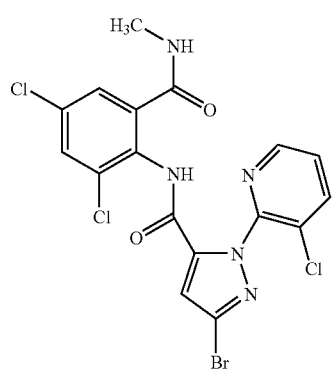
(II-1-12)
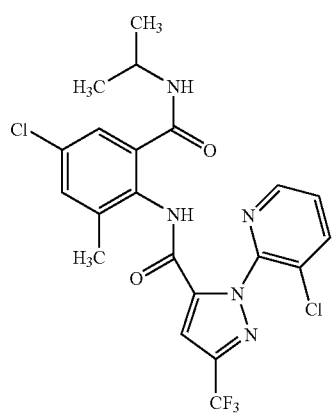
(II-1-13)
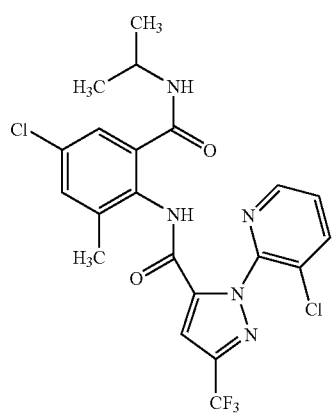
(II-1-15)
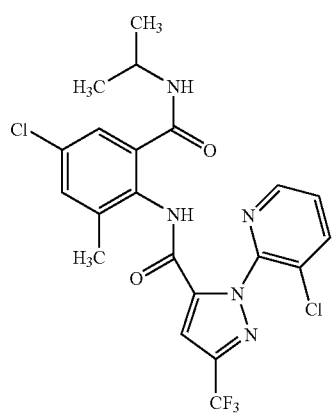
(II-1-16)

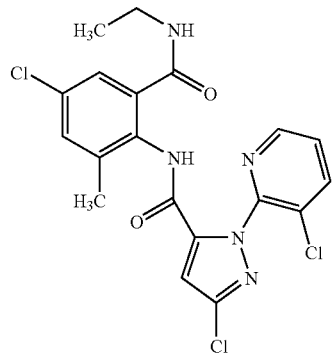
(II-1-19)
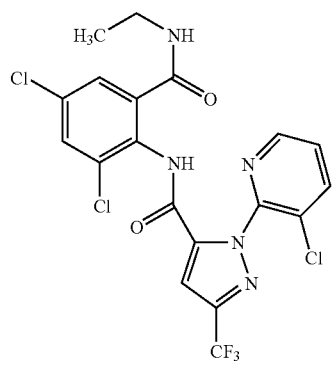
(II-1-21)
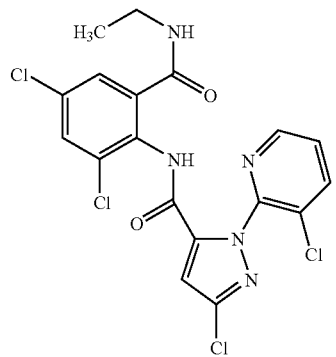
(II-1-22)
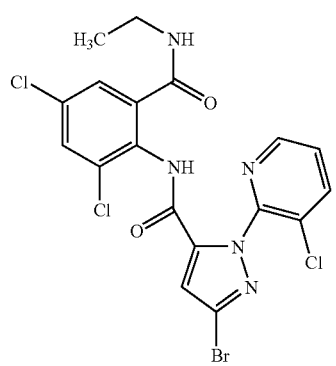
(II-1-23)
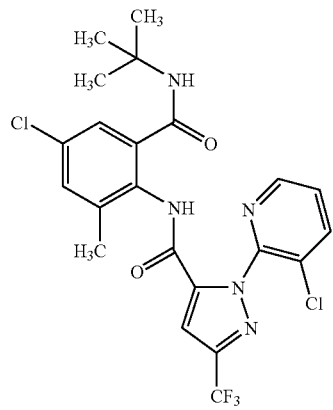
(II-1-24)
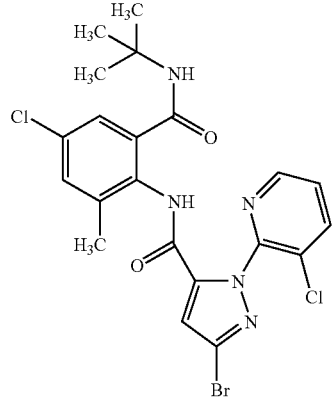
(II-1-26)
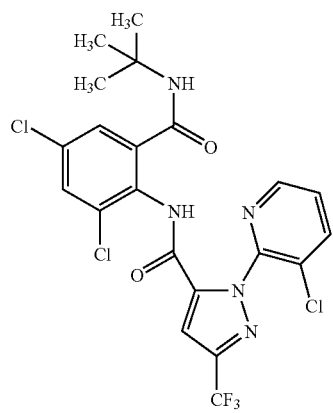
(II-1-27)
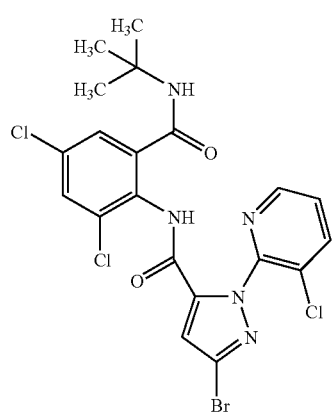
(II-1-29)

(II-1-30)
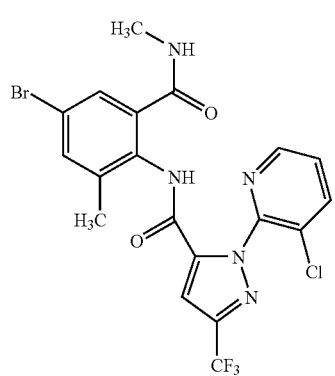
(II-1-31)
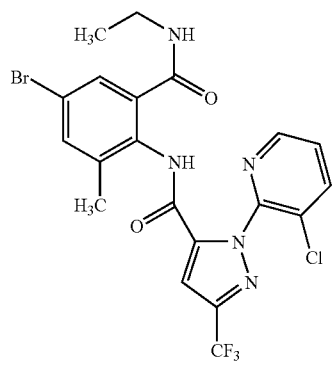
(II-1-32)
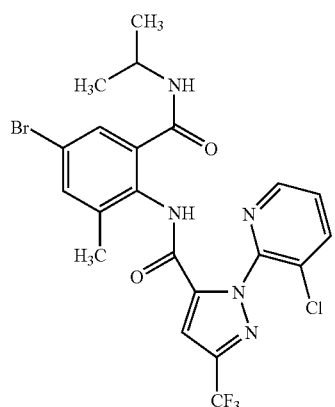
(II-1-33)
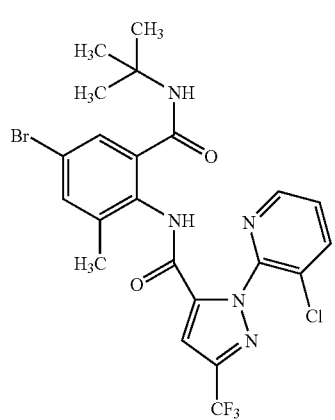
(II-1-38)
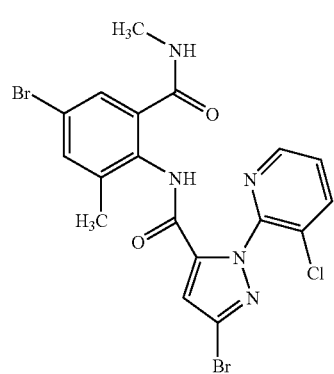
(II-1-39)
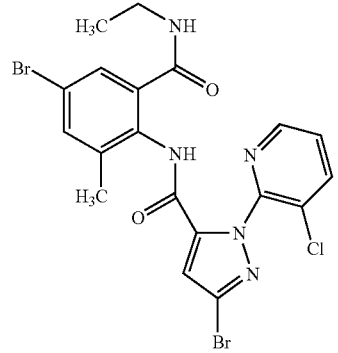
(II-1-40)
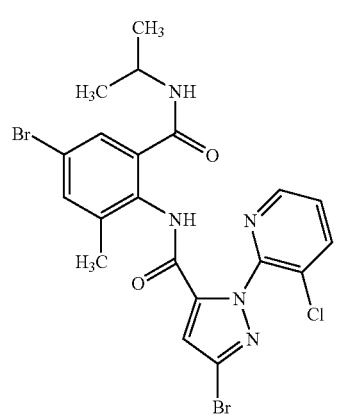
(II-1-42)
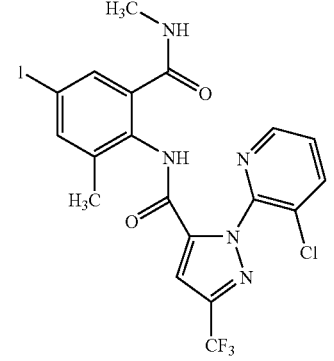

(II-1-43)
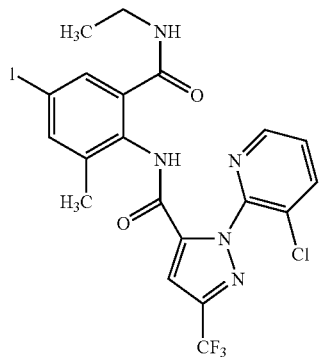
(II-1-44)
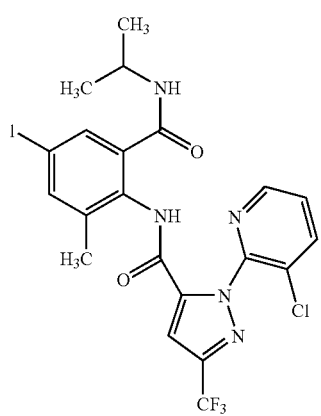
(II-1-50)
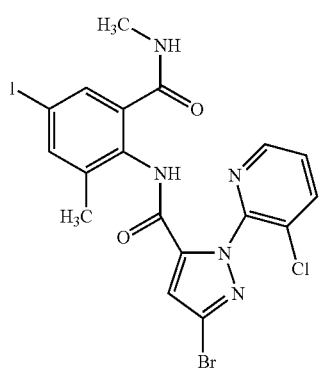
(II-1-51)
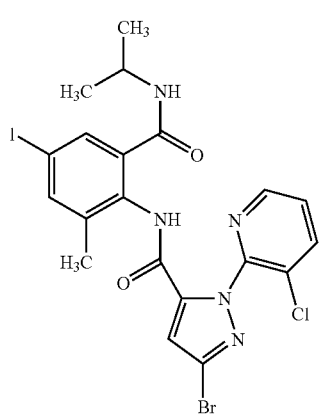
(II-1-52)
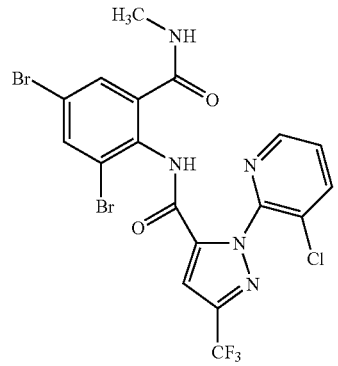
(II-1-53)
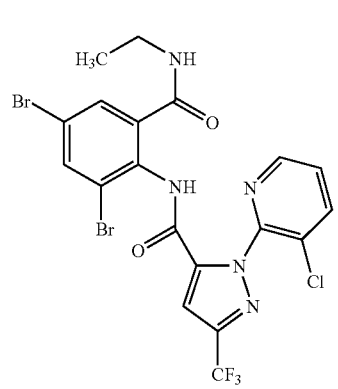
(II-1-54)
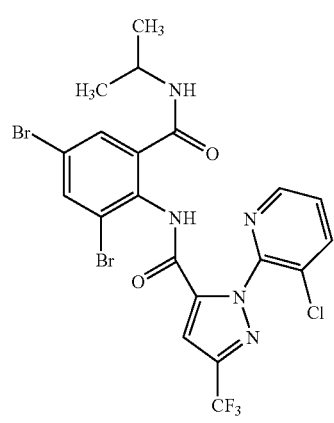
(II-1-55)
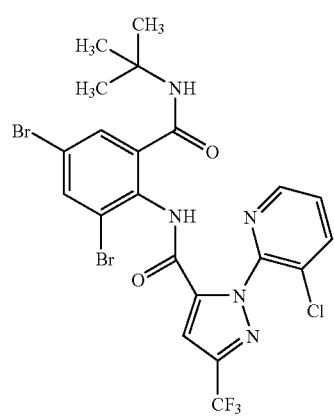

(II-1-56) 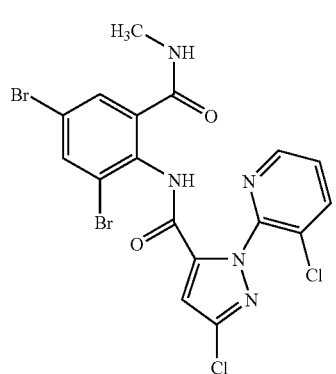
(II-1-57) 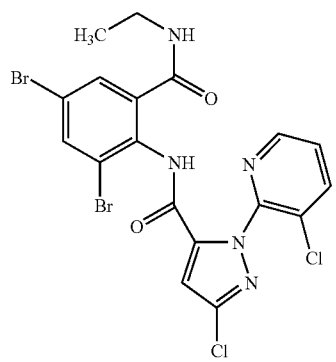
(II-1-58) 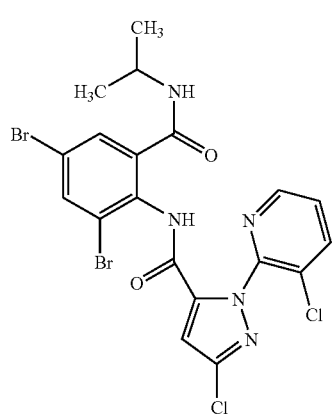
(II-1-60) 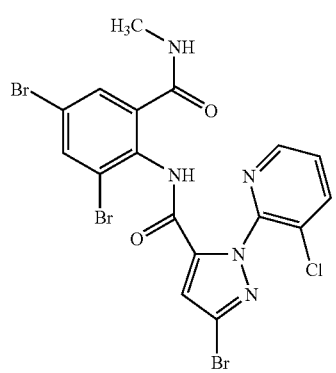
(II-1-61) 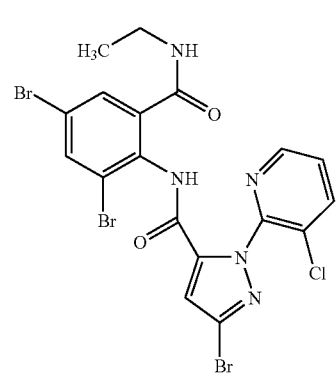
(II-1-62) 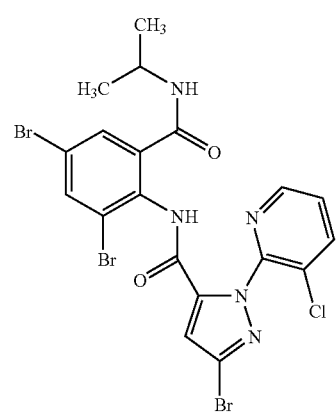
(II-1-64) 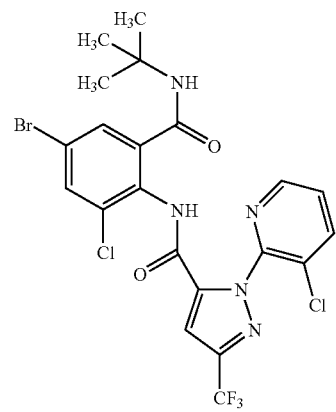
(II-1-65) 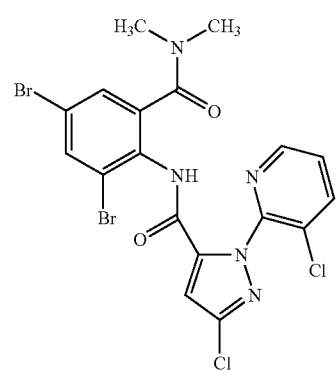

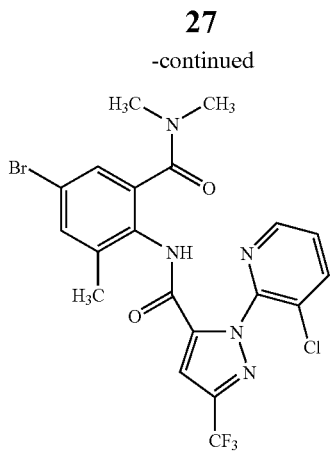
(II-1-66)

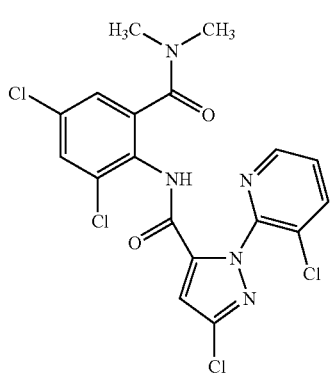
(II-1-67)

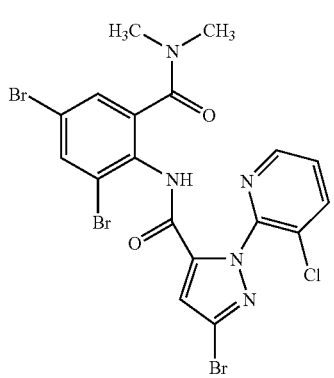
(II-1-68)

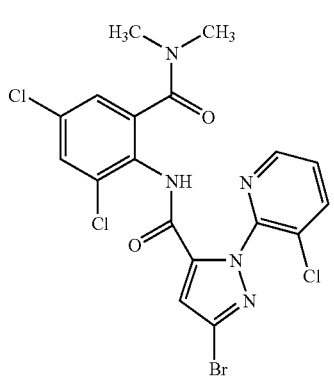
(II-1-69)

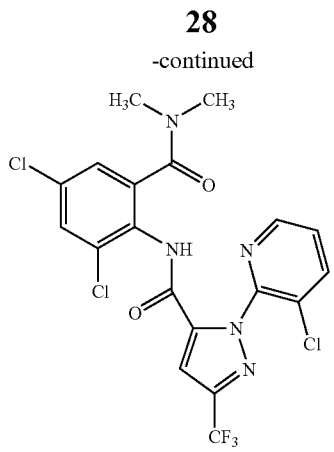
(II-1-70)

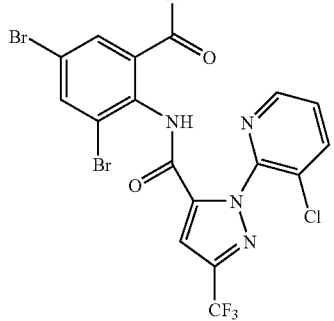
(II-1-71)

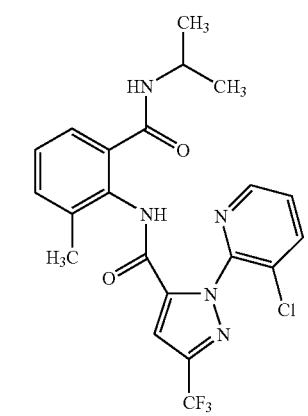
(II-1-72)

and also an active compound of the formula (I) (group 1) or of group 2 selected from the compounds (2-1) to (2-7).

Emphasis is given to active compound combinations comprising the compound of the formula (II-1-9) and the stated active compound of the formula (I) (group 1) or of group 2:

a) Active compound combinations comprising (II-1-9) and (I-a-4).

b) Active compound combinations comprising (II-1-9) and (2-2) buprofezin.

c) Active compound combinations comprising (II-1-9) and (2-6) flonicamid.

d) Active compound combinations comprising (II-1-9) and (2-7) pirimicarb.

Emphasis is given to the following specifically stated active compound combinations (2-component mixtures) comprising one compound of the formula (I) and one compound of the formula (II-1) or of group 2:

| No. | Active compound combination comprising |
|---|---|
| 1a) | (I-a-4) and (II-1-1) |
| 1b) | (2-2) buprofezin and (II-1-1) |
| 1c) | (2-6) flonicamid and (II-1-1) |
| 1d) | (2-7) pirimicarb and (II-1-1) |
| 2a) | (I-a-4) and (II-1-2) |
| 2b) | (2-2) buprofezin and (II-1-2) |
| 2c) | (2-6) flonicamid and (II-1-2) |
| 2d) | (2-7) pirimicarb and (II-1-2) |
| 3a) | (I-a-4) and (II-1-3) |
| 3b) | (2-2) buprofezin and (II-1-3) |
| 3c) | (2-6) flonicamid and (II-1-3) |
| 3d) | (2-7) pirimicarb and (II-1-3) |
| 4a) | (I-a-4) and (II-1-4) |
| 4b) | (2-2) buprofezin and (II-1-4) |
| 4c) | (2-6) flonicamid and (II-1-4) |
| 4d) | (2-7) pirimicarb and (II-1-4) |
| 5a) | (I-a-4) and (II-1-5) |
| 5b) | (2-2) buprofezin and (II-1-5) |
| 5c) | (2-6) flonicamid and (II-1-5) |
| 5d) | (2-7) pirimicarb and (II-1-5) |
| 6a) | (I-a-4) and (II-1-6) |
| 6b) | (2-2) buprofezin and (II-1-6) |
| 6c) | (2-6) flonicamid and (II-1-6) |
| 6d) | (2-7) pirimicarb and (II-1-6) |
| 7a) | (I-a-4) and (II-1-7) |
| 7b) | (2-2) buprofezin and (II-1-7) |
| 7c) | (2-6) flonicamid and (II-1-7) |
| 7d) | (2-7) pirimicarb and (II-1-7) |
| 8a) | (I-a-4) and (II-1-8) |
| 8b) | (2-2) buprofezin and (II-1-8) |
| 8c) | (2-6) flonicamid and (II-1-8) |
| 8d) | (2-7) pirimicarb and (II-1-8) |
| 9a) | (I-a-4) and (II-1-9) |
| 9b) | (2-2) buprofezin and (II-1-9) |
| 9c) | (2-6) flonicamid and (II-1-9) |
| 9d) | (2-7) pirimicarb and (II-1-9) |
| 10a) | (I-a-4) and (II-1-11) |
| 10b) | (2-2) buprofezin and (II-1-11) |
| 10c) | (2-6) flonicamid and (II-1-11) |
| 10d) | (2-7) pirimicarb and (II-1-11) |
| 11a) | (I-a-4) and (II-1-12) |
| 11b) | (2-2) buprofezin and (II-1-12) |
| 11c) | (2-6) flonicamid and (II-1-12) |
| 11d) | (2-7) pirimicarb and (II-1-12) |
| 12a) | (I-a-4) and (II-1-13) |
| 12b) | (2-2) buprofezin and (II-1-13) |
| 12c) | (2-6) flonicamid and (II-1-13) |
| 12d) | (2-7) pirimicarb and (II-1-13) |
| 13a) | (I-a-4) and (II-1-15) |
| 13b) | (2-2) buprofezin and (II-1-15) |
| 13c) | (2-6) flonicamid and (II-1-15) |
| 13d) | (2-7) pirimicarb and (II-1-15) |
| 14a) | (I-a-4) and (II-1-16) |
| 14b) | (2-2) buprofezin and (II-1-16) |
| 14c) | (2-6) flonicamid and (II-1-16) |
| 14d) | (2-7) pirimicarb and (II-1-16) |
| 15a) | (I-a-4) and (II-1-19) |
| 15b) | (2-2) buprofezin and (II-1-19) |
| 15c) | (2-6) flonicamid and (II-1-19) |
| 15d) | (2-7) pirimicarb and (II-1-19) |
| 16a) | (I-a-4) and (II-1-21) |
| 16b) | (2-2) buprofezin and (II-1-21) |
| 16c) | (2-6) flonicamid and (II-1-21) |
| 16d) | (2-7) pirimicarb and (II-1-21) |
| 17a) | (I-a-4) and (II-1-22) |
| 17b) | (2-2) buprofezin and (II-1-22) |
| 17c) | (2-6) flonicamid and (II-1-22) |
| 17d) | (2-7) pirimicarb and (II-1-22) |
| 18a) | (I-a-4) and (II-1-23) |
| 18b) | (2-2) buprofezin and (II-1-23) |
| 18c) | (2-6) flonicamid and (II-1-23) |
| 18d) | (2-7) pirimicarb and (II-1-23) |
| 19a) | (I-a-4) and (II-1-24) |
| 19b) | (2-2) buprofezin and (II-1-24) |
| 19c) | (2-6) flonicamid and (II-1-24) |
| 19d) | (2-7) pirimicarb and (II-1-24) |
| 20a) | (I-a-4) and (II-1-26) |
| 20b) | (2-2) buprofezin and (II-1-26) |
| 20c) | (2-6) flonicamid and (II-1-26) |
| 20d) | (2-7) pirimicarb and (II-1-26) |
| 21a) | (I-a-4) and (II-1-27) |
| 21b) | (2-2) buprofezin and (II-1-27) |
| 21c) | (2-6) flonicamid and (II-1-27) |
| 21d) | (2-7) pirimicarb and (II-1-27) |
| 22a) | (I-a-4) and (II-1-29) |
| 22b) | (2-2) buprofezin and (II-1-29) |
| 22c) | (2-6) flonicamid and (II-1-29) |
| 22d) | (2-7) pirimicarb and (II-1-29) |
| 23a) | (I-a-4) and (II-1-30) |
| 23b) | (2-2) buprofezin and (II-1-30) |
| 23c) | (2-6) flonicamid and (II-1-30) |
| 23d) | (2-7) pirimicarb and (II-1-30) |
| 24a) | (I-a-4) and (II-1-31) |
| 24b) | (2-2) buprofezin and (II-1-31) |
| 24c) | (2-6) flonicamid and (II-1-31) |
| 24d) | (2-7) pirimicarb and (II-1-31) |
| 25a) | (I-a-4) and (II-1-32) |
| 25b) | (2-2) buprofezin and (II-1-32) |
| 25c) | (2-6) flonicamid and (II-1-32) |
| 25d) | (2-7) pirimicarb and (II-1-32) |
| 26a) | (I-a-4) and (II-1-33) |
| 26b) | (2-2) buprofezin and (II-1-33) |
| 26c) | (2-6) flonicamid and (II-1-33) |
| 26d) | (2-7) pirimicarb and (II-1-33) |
| 27a) | (I-a-4) and (II-1-38) |
| 27b) | (2-2) buprofezin and (II-1-38) |
| 27c) | (2-6) flonicamid and (II-1-38) |
| 27d) | (2-7) pirimicarb and (II-1-38) |
| 28a) | (I-a-4) and (II-1-39) |
| 28b) | (2-2) buprofezin and (II-1-39) |
| 28c) | (2-6) flonicamid and (II-1-39) |
| 28d) | (2-7) pirimicarb and (II-1-39) |
| 29a) | (I-a-4) and (II-1-40) |
| 29b) | (2-2) buprofezin and (II-1-40) |
| 29c) | (2-6) flonicamid and (II-1-40) |
| 29d) | (2-7) pirimicarb and (II-1-40) |
| 30a) | (I-a-4) and (II-1-42) |
| 30b) | (2-2) buprofezin and (II-1-42) |
| 30c) | (2-6) flonicamid and (II-1-42) |
| 30d) | (2-7) pirimicarb and (II-1-42) |
| 31a) | (I-a-4) and (II-1-43) |
| 31b) | (2-2) buprofezin and (II-1-43) |
| 31c) | (2-6) flonicamid and (II-1-43) |
| 31d) | (2-7) pirimicarb and (II-1-43) |
| 32a) | (I-a-4) and (II-1-44) |
| 32b) | (2-2) buprofezin and (II-1-44) |
| 32c) | (2-6) flonicamid and (II-1-44) |
| 32d) | (2-7) pirimicarb and (II-1-44) |
| 33a) | (I-a-4) and (II-1-50) |
| 33b) | (2-2) buprofezin and (II-1-50) |
| 33c) | (2-6) flonicamid and (II-1-50) |
| 33d) | (2-7) pirimicarb and (II-1-50) |
| 34a) | (I-a-4) and (II-1-51) |
| 34b) | (2-2) buprofezin and (II-1-51) |
| 34c) | (2-6) flonicamid and (II-1-51) |
| 34d) | (2-7) pirimicarb and (II-1-51) |
| 35a) | (I-a-4) and (II-1-52) |
| 35b) | (2-2) buprofezin and (II-1-52) |
| 35c) | (2-6) flonicamid and (II-1-52) |
| 35d) | (2-7) pirimicarb and (II-1-52) |
| 36a) | (I-a-4) and (II-1-53) |
| 36b) | (2-2) buprofezin and (II-1-53) |
| 36c) | (2-6) flonicamid and (II-1-53) |
| 36d) | (2-7) pirimicarb and (II-1-53) |
| 37a) | (I-a-4) and (II-1-54) |
| 37b) | (2-2) buprofezin and (II-1-54) |
| 37c) | (2-6) flonicamid and (II-1-54) |
| 37d) | (2-7) pirimicarb and (II-1-54) |
| 38a) | (I-a-4) and (II-1-55) |
| 38b) | (2-2) buprofezin and (II-1-55) |
| 38c) | (2-6) flonicamid and (II-1-55) |
| 38d) | (2-7) pirimicarb and (II-1-55) |
| 39a) | (I-a-4) and (II-1-56) |
| 39b) | (2-2) buprofezin and (II-1-56) |

| No. | Active compound combination comprising |
|---|---|
| 39c) | (2-6) flonicamid and (II-1-56) |
| 39d) | (2-7) pirimicarb and (II-1-56) |
| 40a) | (I-a-4) and (II-1-57) |
| 40b) | (2-2) buprofezin and (II-1-57) |
| 40c) | (2-6) flonicamid and (II-1-57) |
| 40d) | (2-7) pirimicarb and (II-1-57) |
| 41a) | (I-a-4) and (II-1-58) |
| 41b) | (2-2) buprofezin and (II-1-58) |
| 41c) | (2-6) flonicamid and (II-1-58) |
| 41d) | (2-7) pirimicarb and (II-1-58) |
| 42a) | (I-a-4) and (II-1-60) |
| 42b) | (2-2) buprofezin and (II-1-60) |
| 42c) | (2-6) flonicamid and (II-1-60) |
| 42d) | (2-7) pirimicarb and (II-1-60) |
| 43a) | (I-a-4) and (II-1-61) |
| 43b) | (2-2) buprofezin and (II-1-61) |
| 43c) | (2-6) flonicamid and (II-1-61) |
| 43d) | (2-7) pirimicarb and (II-1-61) |
| 44a) | (I-a-4) and (II-1-62) |
| 44b) | (2-2) buprofezin and (II-1-62) |
| 44c) | (2-6) flonicamid and (II-1-62) |
| 44d) | (2-7) pirimicarb and (II-1-62) |
| 45a) | (I-a-4) and (II-1-64) |
| 45b) | (2-2) buprofezin and (II-1-64) |
| 45c) | (2-6) flonicamid and (II-1-64) |
| 45d) | (2-7) pirimicarb and (II-1-64) |
| 46a) | (I-a-4) and (II-1-65) |
| 46b) | (2-2) buprofezin and (II-1-65) |
| 46c) | (2-6) flonicamid and (II-1-65) |
| 46d) | (2-7) pirimicarb and (II-1-65) |
| 47a) | (I-a-4) and (II-1-66) |
| 47b) | (2-2) buprofezin and (II-1-66) |
| 47c) | (2-6) flonicamid and (II-1-66) |
| 47d) | (2-7) pirimicarb and (II-1-66) |
| 48a) | (I-a-4) and (II-1-67) |
| 48b) | (2-2) buprofezin and (II-1-67) |
| 48c) | (2-6) flonicamid and (II-1-67) |
| 48d) | (2-7) pirimicarb and (II-1-67) |
| 49a) | (I-a-4) and (II-1-68) |
| 49b) | (2-2) buprofezin and (II-1-68) |
| 49c) | (2-6) flonicamid and (II-1-68) |
| 49d) | (2-7) pirimicarb and (II-1-68) |
| 50a) | (I-a-4) and (II-1-69) |
| 50b) | (2-2) buprofezin and (II-1-69) |
| 50c) | (2-6) flonicamid and (II-1-69) |
| 50d) | (2-7) pirimicarb and (II-1-69) |
| 51a) | (I-a-4) and (II-1-70) |
| 51b) | (2-2) buprofezin and (II-1-70) |
| 51c) | (2-6) flonicamid and (II-1-70) |
| 51d) | (2-7) pirimicarb and (II-1-70) |
| 52a) | (I-a-4) and (II-1-71) |
| 52b) | (2-2) buprofezin and (II-1-71) |
| 52c) | (2-6) flonicamid and (II-1-71) |
| 52d) | (2-7) pirimicarb and (II-1-71) |
| 53a) | (I-a-4) and (II-1-72) |
| 53b) | (2-2) buprofezin and (II-1-72) |
| 53c) | (2-6) flonicamid and (II-1-72) |
| 53d) | (2-7) pirimicarb and (II-1-72) |

However, the general or preferred radical definitions or illustrations given above can also be combined with one another as desired, i.e. including combinations between the respective ranges and preferred ranges. They apply both to the end products and, correspondingly, to precursors and intermediates.

Preference according to the invention is given to active compound combinations comprising the compounds of the formula (I) or a compound of group 2 and also at least one compound of the formula (II) where the individual radicals are a combination of the meanings given above as being preferred (preferable).

Particular preference according to the invention is given to active compound combinations comprising the compounds of the formula (I) or a compound of group 2 and also at least one compound of the formula (II) where the individual radicals are a combination of the meanings given above as being particularly preferred.

Very particular preference according to the invention is given to active compound combinations comprising the compounds of the formula (I) or a compound of group 2 and also at least one compound of the formula (II) where the individual radicals are a combination of the meanings given above as being very particularly preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals may be mono- or polysubstituted, where in the case of polysubstitution the substituents can be identical or different.

In addition, the active compound combinations may also comprise further fungicidally, acaricidally or insecticidally active co-components.

If the active compounds in the active compound combinations according to the invention are present in certain weight ratios, the synergistic effect is particularly pronounced. The mixing ratios required for finding the synergism are not necessarily the preferred mixing ratios relevant for 100% activity. However, the weight ratios of the active compounds in the active compound combinations can be varied within a relatively wide range. In general, the combinations according to the invention comprise active compounds of the formula (I) or a compound of group 2 and the mixing partner of the formula (II) in the stated preferred and particularly preferred mixing ratios:

The mixing ratios are based on weight ratios. The ratio is to be understood as meaning active compound of the formula (I): mixing partner

| Mixing partner | Preferred mixing ratio | Particularly preferred mixing ratio |
|---|---|---|
| (I-a-4) | 10:1 to 1:10 | 5:1 to 1:5 |
| Amitraz | 5:1 to 1:20 | 1:1 to 1:10 |
| Buprofezin | 10:1 to 1:10 | 5:1 to 1:5 |
| Pymetrozine | 10:1 to 1:10 | 5:1 to 1:5 |
| Pyriproxyphen | 10:1 to 1:10 | 5:1 to 1:5 |
| Triazamate | 10:1 to 1:10 | 5:1 to 1:5 |
| Flonicamid | 10:1 to 1:10 | 5:1 to 1:5 |
| Pirimicarb | 10:1 to 1:10 | 5:1 to 1:5 |

The active compound combinations of the invention are suitable for controlling animal pests, preferably arthropods and nematodes, in particular insects and arachnids, found in agriculture, in animal health, in forests, in gardens and leisure facilities, in the protection of stored products and materials and in the hygiene sector, while exhibiting good tolerability to plants, low toxicity to warm-blooded species and good environmental compatibility. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina*.

From the order of the Collembola, for example, *Onychiurus armatus*.

From the order of the Orthoptera, for example, *Acheta domesticus, Gryllotalpa* spp., *Locusta migratoria migratorioides, Melanoplus* spp., *Schistocerca gregaria*.

From the order of the Blattaria, for example, *Blatta orientalis, Periplaneta americana, Leucophaea maderae, Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella accidentalis*.

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniiarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrofica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptus oryzophilus*.

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compound combinations of the invention of the compounds of the formula (I) and at least one compound 1 to 15 are particularly suitable for controlling "biting" pests. These include, in particular, the following pests:

From the order of the Lepidoptera for example, *Pectinophora gossypiella, Bupalus piniiarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus*.

The active compound combinations of the invention of the compounds of the formula (I) and at least one compound 5 to 8 are additionally particularly suitable for controlling "sucking" pests. These include, in particular, the following pests:

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

The active compound combinations of the invention have, in particular, excellent activity against caterpillars, beetle larvae, spider mites, aphids and leaf-mining flies.

The active compound combinations of the invention can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations of the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas, and substances produced by microorganisms, inter alia.

Mixtures with other known active compounds such as herbicides or with fertilizers and growth regulators are also possible.

When used as insecticides, the active compound combinations of the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations of the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp.; *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the orders of the Meta- and Mesostigmata, for example, *Argas* spp., *Ornithodonis* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp.,

*Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations of the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations of the invention.

The active compound combinations of the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising molded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10,000-fold dilution, or they may be used as a chemical dip.

Moreover, it has been found that the active compound combinations of the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pectinicornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus*.

Dermapterans such as *Sirex juvencus, Urocerus gigas, Urocerus gigas taignus, Urocerus augur*.

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*.

Bristle-tails such as *Lepisma saccharina*.

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition of the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound of the invention in a concentration of 0.0001 to 95% by weight, in particular 0.001 to 60% by weight The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odor-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl)adipate, stearates such as butyl stearate or amyl stearate, oleates such as butyl oleate, glycerol ethers or higher-molecular-weight glycol ethers, glycerol esters and p-toluenesulfonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations of the invention can at the same time be employed for protecting objects which come into contact with saltwater or brackish water, such as hulls, screens, nets, buildings, moorings and signaling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., fouling by sessile Entomostraka groups, which come under the generic term *Cirripedia* (cirriped crustaceans), is of particular importance.

Surprisingly, it has now been found that the active compound combinations of the invention have an outstanding antifouling action.

Using the active compound combinations of the invention allows the use of heavy metals such as, for example, in bis(trialkyltin) sulfides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulfide, antimony oxide, polymeric butyl titanate, phenyl (bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combination with the antifouling compositions according to the invention are:
algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as fentin acetate, metaldehyde, methiocarb, niclosamid, thiodicarb and trimethacarb;
or conventional antifouling active compounds such as 4,5-dichloro-2-octyl-4-isothiazolin-3-one, diiodomethylparatryl sulfone, 2-(N,N-dimethylthiocarbamoylthio)-5-nitrothiazyl, potassium, copper, sodium and zinc salts of 2-pyridinethiol 1-oxide, pyridine/triphenylborane, tetrabutyldistannoxane, 2,3,5,6-tetrachloro-4-methylsulfonyl)pyridine, 2,4,5,6-tetrachloroisophthalonitrile, tetramethylthiuram disulfide and 2,4,6-trichlorophenylmaleimide.

The antifouling compositions used comprise the active compound combinations of the invention in a concentration of 0.001 to 50% by weight, in particular 0.01 to 20% by weight.

Moreover, the antifouling compositions of the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds of the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds of the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides filis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment of the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are particularly emphasized are the increased defense of the plants against insects, arachnids, nematodes and worms by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defense of plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combination with one another in the transgenic plants. Examples of "Bt plants". which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be developed genetic traits, which plants will be developed and/or marketed in the future.

The plants listed can be treated according to the invention in a particularly advantageous manner with the active compound mixtures of the invention. The preferred ranges stated above for the mixtures also apply to the treatment of these plants. Particular emphasis is given to the treatment of plants with the mixtures specifically mentioned in the present text.

The good insecticidal and acaricidal action of the active compound combinations of the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using "Colby's formula" (cf. S. R. Colby, "Calculating Synergistic and Antagonistic Responses of Herbicide Combinations", Weeds 1967, 15, 20-22):

If

X is the kill rate, expressed as a percentage of the untreated control, when employing active compound A at an application rate of m g/ha or in a concentration of m ppm, Y is the kill rate, expressed as a percentage of the untreated control, when employing active compound B at an application rate of n g/ha or in a concentration of n ppm and E is the kill rate, expressed as a percentage of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the action of the combination is superadditive, i.e. a synergistic effect is present. In this case, the actually observed kill rate must exceed the value calculated using the above formula for the expected kill rate (E).

USE EXAMPLES

Example A

| *Aphis gossypii* test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time; the kill in % is determined. 100% means that all aphids have been killed; 0% means that none of the aphids have been killed. The determined kill rates are entered into Colby's formula (see page 41).

In this test, for example, the following active compound combination in accordance with the present application shows a synergistically enhanced activity compared to the active compounds applied on their own:

TABLE A1

Plant-damaging insects
*Aphis gossypii* test

| Active compounds | Concentration of active compound in ppm | Kill rate in % after 7$^d$ found* | calc.** |
|---|---|---|---|
| 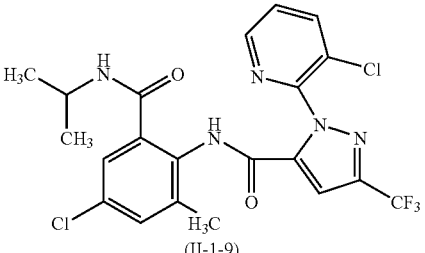 (II-1-9) | 4 | 20 | |
| 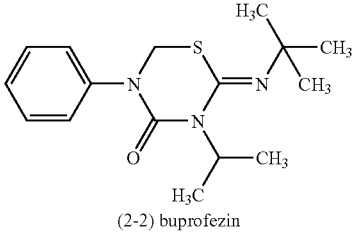 [SMILES: CC(C)N1C(=O)N(c2ccccc2)CS/C1=N\C(C)(C)C] (2-2) buprofezin | 20 | 0 | |
| (II-1-9) + (2-2)buprofezin(1:5) | 4 + 20 | 40 | 20 |

*found = activity found
**calc. = activity calculated using Colby's formula

TABLE A2

Plant-damaging inserts
*Aphis gossypii* test

| Active compounds | Concentration of active compound in ppm | Kill rate in % after 6$^d$ found* | calc.** |
|---|---|---|---|
| 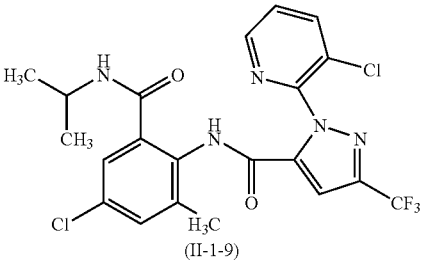 (II-1-9) | 20 | 55 | |
| 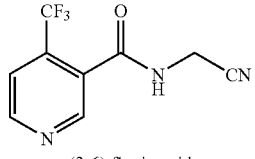 (2-6) flonicamid | 20 | 40 | |
| (II-1-9) + (2-6)flonicamid(1:1) | 20 + 20 | 99 | 73 |

*found = activity found
**calc. = activity calculated using Colby's formula

Example B

| Myzus persicae test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The determined kill rates are entered into Colby's formula (see on page 41).

In this test, for example, the following active compound combination in accordance with the present application shows a synergistically enhanced activity compared to the active compounds applied on their own:

TABLE B1

Plant-damaging insects
*Myzus persicae* test

| Active compounds | Concentration of active compound in ppm | Kill rate in % after $6^d$ | |
|---|---|---|---|
| | | found* | calc.** |
| (II-1-9) | 4 | 30 | |
| (I-a-4) | 4 | 80 | |
| (II-1-9) + (I-a-4) (1:1) | 4 + 4 | 98 | 86 |

*found = activity found
**calc. = activity calculated using Colby's formula

TABLE B2

Plant-damaging insects
*Myzus persicae* test

| Active compounds | Concentration of active compound in ppm | Kill rate in % after 6$^d$ found* | calc.** |
|---|---|---|---|
| 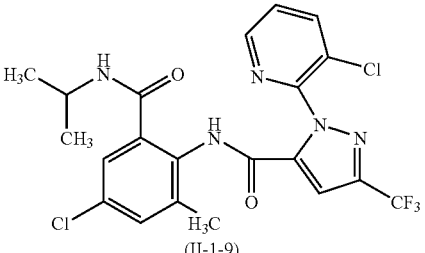 (II-1-9) | 4 | 0 | |
| 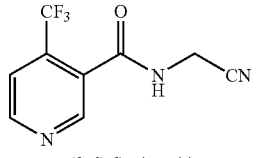 (2-6) flonicamid | 4 | 40 | |
| (II-1-9) + (2-6)flonicamid(1:1) | 4 + 4 | 95 | 40 |

*found = activity found
**calc. = activity calculated using Colby's formula

Example C

| *Phaedon cochleariae* larvae test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are entered into Colby's formula (see page 41).

In this test, for example, the following active compound combination in accordance with the present application shows a synergistically enhanced activity compared to the active compounds applied on their own:

TABLE C1

Plant-damaging insects
*Phaedon cochleariae* larvae test

| Active compounds | Concentration of active compound in ppm | Kill rate in % after 3$^d$ found* | calc.** |
|---|---|---|---|
| 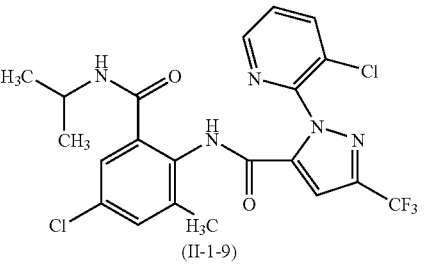 [SMILES: Cc1cc(Cl)cc(C(=O)NC(C)C)c1NC(=O)c1cc(C(F)(F)F)nn1-c1ncccc1Cl] (II-1-9) | 0.16 | 5 | |

TABLE C1-continued

Plant-damaging insects
*Phaedon cochleariae larvae* test

| Active compounds | Concentration of active compound in ppm | Kill rate in % after 3$^d$ | |
|---|---|---|---|
| | | found* | calc.** |
| 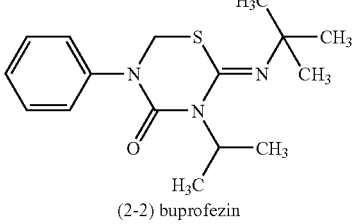 (2-2) buprofezin | 100 | 20 | |
| (II-1-9) + (2-2) buprofezin (1:625) | 0.16 + 100 | 65 | 24 |

*found = activity found
**calc. = activity calculated using Colby's formula

TABLE C2

Plant-damaging insects
*Phaedon cochleariae larvae* test

| Active compounds | Concentration of active compound in ppm | Kill rate in % after 6$^d$ | |
|---|---|---|---|
| | | found* | calc.** |
| 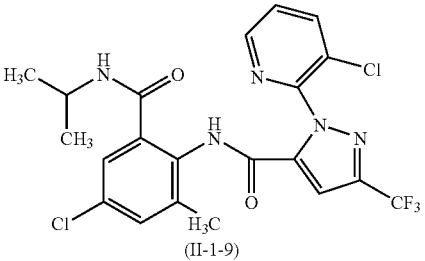 (II-1-9) | 0.16 | 0 | |
| 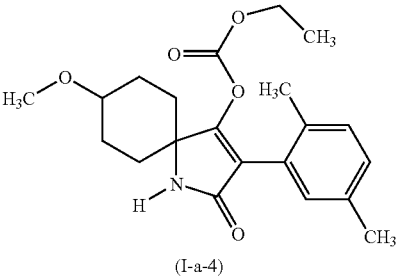 (I-a-4) | 4 | 15 | |
| (II-1-9) + (I-a-4) (1:25) | 0.16 + 4 | 55 | 15 |

*found = activity found
**calc. = activity calculated using Colby's formula

Example D

| *Plutella xylostella* test (resistant strain) | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*, resistant strain) while the leaves are still moist.

After the desired period of time, the kill in % is determined. 100% means that all caterpillars have been killed; 0% means that none of the caterpillars have been killed. The determined kill rates are entered into Colby's formula (see page 41).

In this test, for example, the following active compound combination in accordance with the present application shows a synergistically enhanced activity compared to the active compounds applied on their own:

TABLE D

| Active compounds | Concentration of active compound in ppm | Kill rate in % after $6^d$ | |
|---|---|---|---|
| | | found* | calc.** |
| (II-1-9) | 0.0064 | 0 | |
| (I-a-4) | 0.16 | 0 | |
| (II-1-9) + (I-a-4) (1:25) | 0.0064 + 0.16 | 65 | 0 |

*found = activity found
**calc. = activity calculated using Colby's formula

Example E

| *Spodoptera frugiperda* test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed. The determined kill rates are entered into Colby's formula (see page 41).

In this test, for example, the following active compound combination in accordance with the present application shows a synergistically enhanced activity compared to the active compounds applied on their own:

TABLE E

Plant-damaging insects
*Spodoptera frugiperda* test

| Active compounds | Concentration of active compound in ppm | Kill rate in % after 3$^d$ found* | calc.** |
|---|---|---|---|
| (II-1-9) 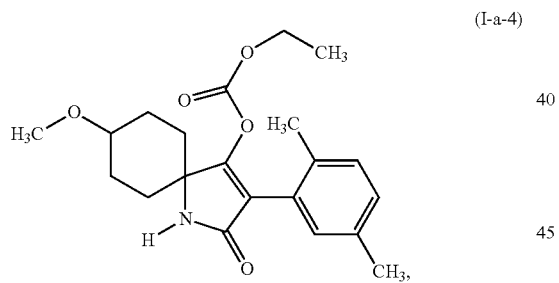 | 0.16 | 45 | |
| (2-6) Flonicamid 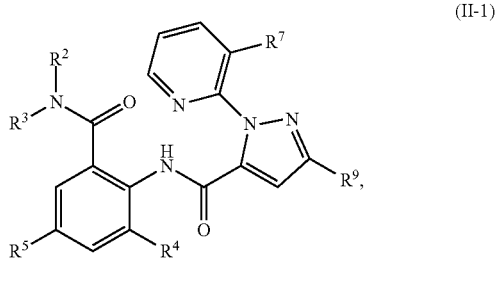 | 100 | 5 | |
| (II-1-9) + (2-6) flonicamid (1:625) | 0.16 + 100 | 100 | 47.75 |

*found = activity found
**calc. = activity calculated using Colby's formula

The invention claimed is:

1. A composition for controlling animal pests comprising a synergistically effective active compound combination of the compound of the formula (I-a-4)

(I-a-4)

or at least one insecticidally active compound (group 2) selected from
(2-2) buprofezin,
(2-6) flonicamid,
(2-7) pirimicarb,
and at least one active compound from the group of the anthranilamides of the formula (II-1)

(II-1)

in which
$R^2$ represents hydrogen or methyl,
$R^3$ represents $C_1$-$C_4$ alkyl,
$R^4$ represents methyl, trifluoromethyl, trifluoromethoxy, fluorine, chlorine, bromine or iodine,
$R^5$ represents hydrogen, fluorine, chlorine, bromine, iodine, trifluoromethyl or trifluoromethoxy,
$R^7$ represents chlorine or bromine, and
$R^9$ represents trifluoromethyl, chlorine, bromine, difluoromethoxy or trifluoroethoxy, wherein the weight ratio of the compound of formula (I-a-4) or the at least one insecticidally active compound (group 2) to the at least one active compound from the group of the anthranilamides is from 10:1 to 1:10.

2. The composition as claimed in claim 1, comprising a synergistically effective active compound combination of the compound of the formula (I-a-4), and at least one compound from the group of the anthranilamides of the formula (II-1).

3. The composition as claimed in claim 1, comprising a synergistically effective active compound combination of the compound pirimicarb, and at least one compound from the group of the anthranilamides of the formula (II-1).

4. A process for preparing a pesticide, comprising mixing the synergistically effective active compound combination as defined in claim 1 with substances selected from the group consisting of extenders, surfactants and mixtures thereof.

5. The composition as claimed in claim 1, wherein said weight ratio is from 5:1 to 1:5.

6. The composition as claimed in claim 1, comprising a synergistically effective active compound combination of the compound (2-2) buprofezin and the compound of the formula (II-1-9)

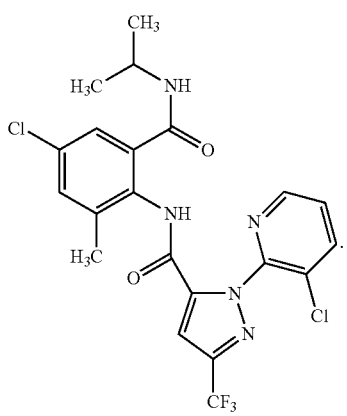

(II-1-9)

7. The composition as claimed in claim 6, wherein the weight ratio of the compound (2-2) buprofezin and the compound of the formula (II-1-9) is 5:1.

8. The composition as claimed in claim 6, comprising a synergistically effective active compound combination of the compound (2-6) flonicamid and the compound of the formula (II-1-9).

9. The composition as claimed in claim 8, wherein the weight ratio of the compound (2-6) flonicamid and the compound of the formula (II-1-9) is 1:1.

10. The composition as claimed in claim 2, wherein said compound from the group of the anthranilamides of the formula (II-1) is the compound of the formula (II-1-9)

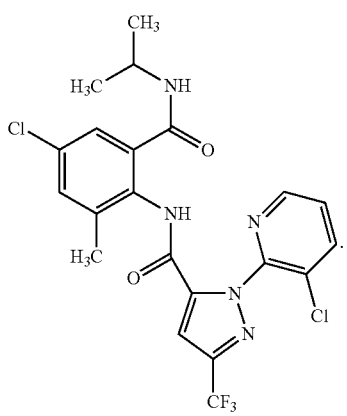

(II-1-9)

11. The composition as claimed in claim 10, wherein the weight ratio of the compound of the formula (I-a-4) and the compound of the formula (II-1-9) is 1:1.

12. The composition as claimed in claim 1, comprising a synergistically effective active compound combination of the compound (2-2) buprofezin and the compound of the formula (II-1-4)

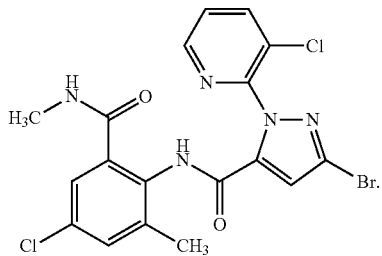

(II-1-4)

13. The composition as claimed in claim 1, comprising a synergistically effective active compound combination of the compound (2-6) flonicamid and the compound of the formula (II-1-4)

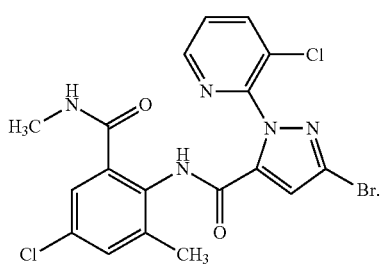

(II-1-4)

14. The composition as claimed in claim 2, wherein said compound from the group of the anthranilamides of the formula (II-1) is the compound of the formula (II-1-4)

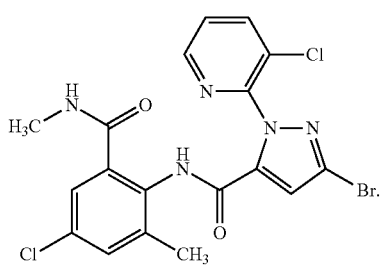

(II-1-4)

* * * * *